United States Patent

Plaia et al.

[11] Patent Number: 5,934,284
[45] Date of Patent: *Aug. 10, 1999

[54] METHOD FOR INCREASING BLOOD FLOW IN VESSELS

[75] Inventors: Mark Plaia, Tigard; Vincent A. Reger, Portland; Gregory N. Nordgren, Wilsonville, all of Oreg.

[73] Assignee: Endovascular Instruments, Inc, Vancouver, Wash.

[*] Notice: This patent is subject to a terminal disclaimer.

[21] Appl. No.: 08/402,789

[22] Filed: Mar. 13, 1995

Related U.S. Application Data

[60] Division of application No. 08/073,002, Jun. 7, 1993, Pat. No. 5,571,169, which is a continuation-in-part of application No. 08/056,224, May 4, 1993, abandoned, which is a continuation of application No. 07/922,115, Jul. 28, 1992, Pat. No. 5,282,484, which is a continuation of application No. 07/616,240, Nov. 20, 1990, abandoned, which is a division of application No. 07/395,500, Aug. 18, 1989, abandoned.

[51] Int. Cl.$^6$ .................................................. A61B 19/00
[52] U.S. Cl. ............................ 128/898; 623/1; 606/159; 606/191
[58] Field of Search ................. 128/898; 623/1; 606/159, 191, 194, 195

[56] References Cited

U.S. PATENT DOCUMENTS

| | | | |
|---|---|---|---|
| 207,932 | 9/1878 | Alvord . | |
| 1,693,545 | 11/1928 | Broersma . | |
| 2,085,368 | 6/1937 | Kendall | 128/341 |
| 3,635,223 | 1/1972 | Klieman | 128/348 |
| 3,730,185 | 5/1973 | Cook et al. | 128/303 |
| 3,788,318 | 1/1974 | Kim et al. | 128/214.4 |
| 3,868,956 | 3/1975 | Alfidi et al. | 128/345 |
| 4,140,126 | 2/1979 | Choudhury | 128/325 |
| 4,281,658 | 8/1981 | Child | 128/341 |
| 4,503,569 | 3/1985 | Dotter . | |
| 4,512,338 | 4/1985 | Balko et al. . | |
| 4,531,512 | 7/1985 | Wolvek et al. . | |

(List continued on next page.)

FOREIGN PATENT DOCUMENTS 1482714  5/1989  U.S.S.R. .

OTHER PUBLICATIONS

Article entitled "Papers of the Society for Clinical Vascular Surgery", *the American Journal of Surgery*, vol. 162, Aug. 1991.
Advertisement introducing Scanlan Endarsector, 1984.
Improved Intrumentation for Endarterectomy, 1980 article entitled "The Hall Arterial Oscillotor Instruction Manual".
Percutaneous Femoropoplitael Graft Placement, Andrew H. Cragg, M.D., Micheal D. Dake, MD, *Radiology 1993*; 187:643–648. Jan. 18, 1993.
Patents, Teresa Riordan, *The New York Times*, Jun. 14, 1994.
Techniques on Rise for Unblocking Arteries, *Salt Lake Tribune*, Science and Medicine section, Thursday, Jun. 17, 1993.
Giovanni et al, Stroke vol. 15, No. 6, 1984, pp. 972–979.
Stedman's Medical Dictionary, 23rd Edition, pp. 77, 122, and 459.

*Primary Examiner*—Paul B. Prebilic
*Attorney, Agent, or Firm*—Foster & Foster

[57] ABSTRACT

A method of enlarging the lumen of a vessel is disclosed, by which an access opening or passageway is provided to the vessel, a head is inserted through the opening and advanced to a constriction within the vessel. The head engages, severs, and removes plaque. A vascular graft lining is inserted into the vessel and to the site of enlargement where it is secured within the vessel at the site of enlargement.

11 Claims, 10 Drawing Sheets

U.S. PATENT DOCUMENTS

| | | | |
|---|---|---|---|
| 4,553,545 | 11/1985 | Maass et al. ............................ 128/341 |
| 4,577,631 | 3/1986 | Kreamer . |
| 4,580,568 | 4/1986 | Gianturco . |
| 4,641,653 | 2/1987 | Rockey . |
| 4,655,771 | 4/1987 | Wallsten . |
| 4,681,110 | 7/1987 | Wiktor . |
| 4,699,611 | 10/1987 | Bowden . |
| 4,705,517 | 11/1987 | DiPisa, Jr. . |
| 4,732,152 | 3/1988 | Wallsten et al. . |
| 4,733,665 | 3/1988 | Palmaz . |
| 4,739,762 | 4/1988 | Palmaz .................................. 128/343 |
| 4,745,919 | 5/1988 | Bundy et al. ........................... 606/159 |
| 4,760,849 | 8/1988 | Kropf . |
| 4,763,653 | 8/1988 | Rockey . |
| 4,772,264 | 9/1988 | Cragg ..................................... 604/158 |
| 4,776,337 | 10/1988 | Palmaz . |
| 4,787,899 | 11/1988 | Lazarus . |
| 4,790,310 | 12/1988 | Ginsberg et al. ...................... 606/159 |
| 4,792,330 | 12/1988 | Lazarus et al. ........................ 604/174 |
| 4,793,348 | 12/1988 | Palmaz .................................. 128/325 |
| 4,795,458 | 1/1989 | Regan . |
| 4,799,479 | 1/1989 | Spears . |
| 4,800,882 | 1/1989 | Gianturco . |
| 4,820,298 | 4/1989 | Leveen et al. . |
| 4,830,003 | 5/1989 | Wolff et al. . |
| 4,848,343 | 7/1989 | Wallsten et al. . |
| 4,856,516 | 8/1989 | Hillstead . |
| 4,877,030 | 10/1989 | Beck et al. . |
| 4,886,062 | 12/1989 | Wiktor . |
| 4,886,500 | 12/1989 | Lazarus .................................. 604/164 |
| 4,889,137 | 12/1989 | Kolobow . |
| 4,899,729 | 2/1990 | Gill et al. . |
| 4,913,141 | 4/1990 | Hillstead . |
| 4,922,905 | 5/1990 | Strecker . |
| 4,923,464 | 5/1990 | DiPisa, Jr. . |
| 4,954,126 | 9/1990 | Wallsten . |
| 4,969,458 | 11/1990 | Wiktor . |
| 4,990,151 | 2/1991 | Wallsten . |
| 4,990,155 | 2/1991 | Wikoff . |
| 4,994,066 | 2/1991 | Voss . |
| 4,994,069 | 2/1991 | Ritchart et al. . |
| 4,994,071 | 2/1991 | MacGregor . |
| 5,002,560 | 3/1991 | Machold et al. . |
| 5,007,926 | 4/1991 | Derbyshire . |
| 5,019,075 | 5/1991 | Spears et al. . |
| 5,019,090 | 5/1991 | Pinchuk . |
| 5,034,001 | 7/1991 | Garrison et al. . |
| 5,035,706 | 7/1991 | Gianturco et al. . |
| 5,037,392 | 8/1991 | Hillstead . |
| 5,037,427 | 8/1991 | Harada et al. . |
| 5,041,126 | 8/1991 | Gianturco . |
| 5,059,211 | 10/1991 | Stack et al. . |
| 5,064,435 | 11/1991 | Porter . |
| 5,071,407 | 12/1991 | Termin et al. . |
| 5,071,424 | 12/1991 | Reger ..................................... 606/159 |
| 5,074,841 | 12/1991 | Ademoric et al. ..................... 606/159 |
| 5,078,720 | 1/1992 | Burton et al. . |
| 5,078,726 | 1/1992 | Kreamer . |
| 5,084,010 | 1/1992 | Plaia et al. .............................. 604/22 |
| 5,085,635 | 2/1992 | Cragg ..................................... 604/96 |
| 5,089,005 | 2/1992 | Harada . |
| 5,089,006 | 2/1992 | Stiles . |
| 5,092,841 | 3/1992 | Spears . |
| 5,100,429 | 3/1992 | Sinofsky et al. . |
| 5,102,417 | 4/1992 | Palmaz . |
| 5,104,399 | 4/1992 | Lazarus . |
| 5,108,366 | 4/1992 | Schatz ..................................... 604/55 |
| 5,108,417 | 4/1992 | Sawyer . |
| 5,116,318 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,536 | 8/1992 | Hillstead . |
| 5,139,480 | 8/1992 | Hickle et al. . |
| 5,147,370 | 9/1992 | McNamara et al. . |
| 5,147,385 | 9/1992 | Beck et al. . |
| 5,151,105 | 9/1992 | Kwan-Gett . |
| 5,156,619 | 10/1992 | Ehrenfeld . |
| 5,156,620 | 10/1992 | Pigott . |
| 5,158,543 | 10/1992 | Lazarus .................................. 604/164 |
| 5,158,545 | 10/1992 | Trudell et al. . |
| 5,160,341 | 11/1992 | Brenneman et al. . |
| 5,161,547 | 11/1992 | Tower et al. . |
| 5,163,958 | 11/1992 | Pinchuk . |
| 5,178,618 | 1/1993 | Kandarpa . |
| 5,180,368 | 1/1993 | Garrison . |
| 5,181,911 | 1/1993 | Shturman . |
| 5,190,058 | 3/1993 | Jones et al. . |
| 5,192,295 | 3/1993 | Danforth et al. . |
| 5,192,297 | 3/1993 | Hull . |
| 5,195,984 | 3/1993 | Schatz . |
| 5,196,024 | 3/1993 | Barath .................................... 606/159 |
| 5,197,977 | 3/1993 | Huffman, Jr. et al. ..................... 623/1 |
| 5,197,978 | 3/1993 | Hess . |
| 5,199,951 | 4/1993 | Spears . |
| 5,201,756 | 4/1993 | Horzewski et al. . |
| 5,201,757 | 4/1993 | Heyn et al. . |
| 5,201,901 | 4/1993 | Harada et al. . |
| 5,207,695 | 5/1993 | Trout III . |
| 5,211,654 | 5/1993 | Kaltenbach . |
| 5,211,658 | 5/1993 | Clouse . |
| 5,213,580 | 5/1993 | Slepian .................................... 623/1 |
| 5,224,945 | 7/1993 | Pannek, Jr. ............................. 606/159 |
| 5,226,909 | 7/1993 | Evans et al. ............................ 606/159 |
| 5,234,451 | 8/1993 | Osypka ................................... 606/159 |
| 5,267,954 | 12/1993 | Nita ........................................ 606/159 |
| 5,282,484 | 2/1994 | Reger ..................................... 128/898 |
| 5,282,824 | 2/1994 | Gianturco ................................... 623/1 |
| 5,342,348 | 8/1994 | Kaplan . |
| 5,358,507 | 10/1994 | Daily . |
| 5,360,443 | 11/1994 | Barone et al. . |
| 5,397,345 | 3/1995 | Lazarus . |
| 5,419,760 | 5/1995 | Narcisco, Jr. ............................ 623/1 |
| 5,571,169 | 11/1996 | Plaia et al. .............................. 623/1 |
| 5,622,188 | 4/1997 | Plaia et al. ............................. 128/898 |

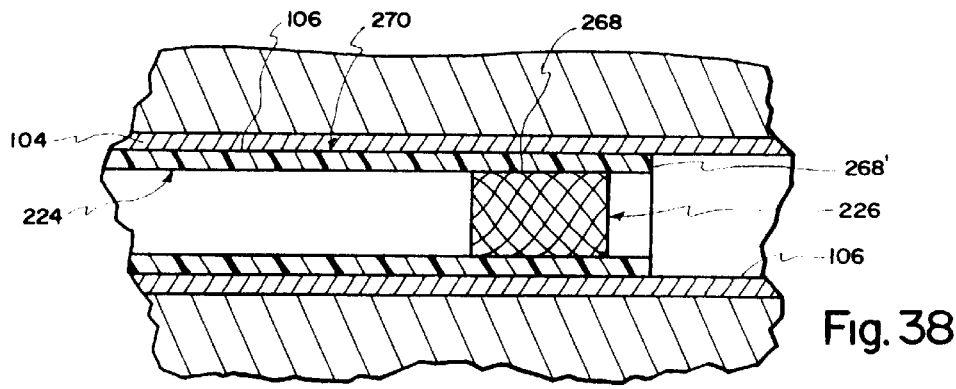
Fig. 38
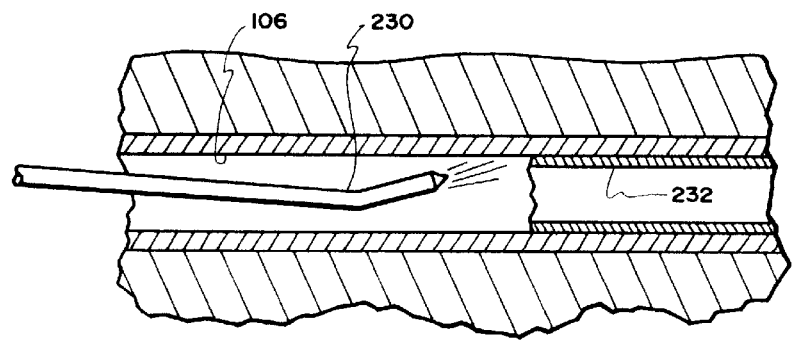
Fig. 39
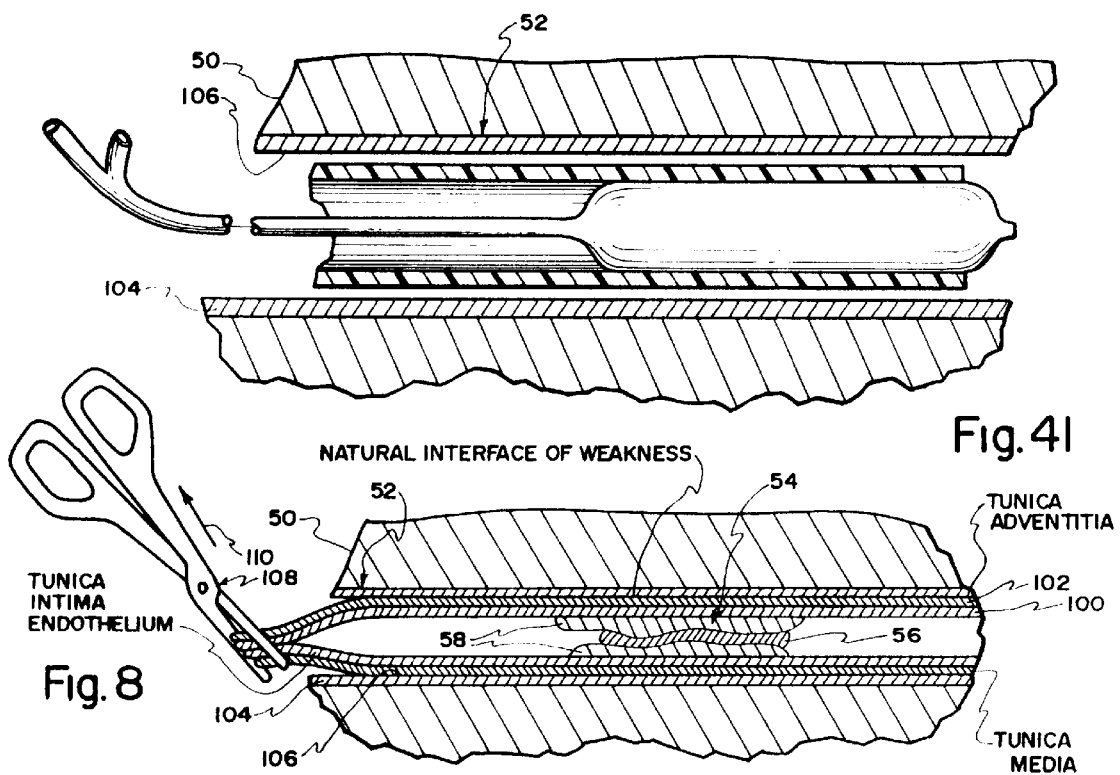
Fig. 41
Fig. 8

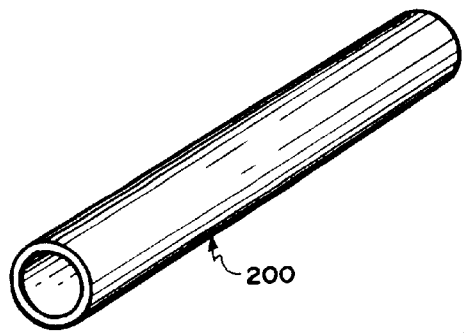
Fig. 16
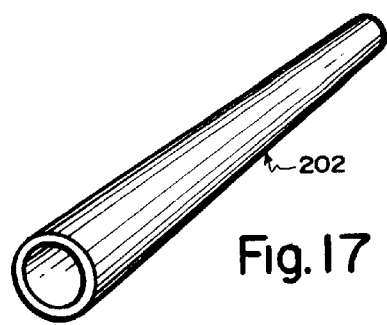
Fig. 17
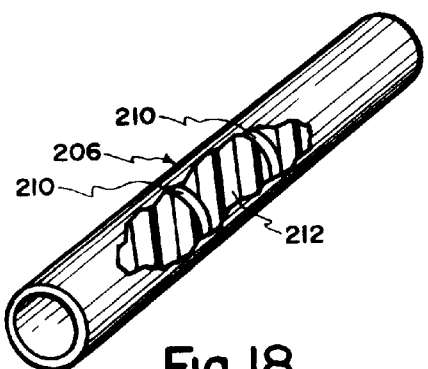
Fig. 18
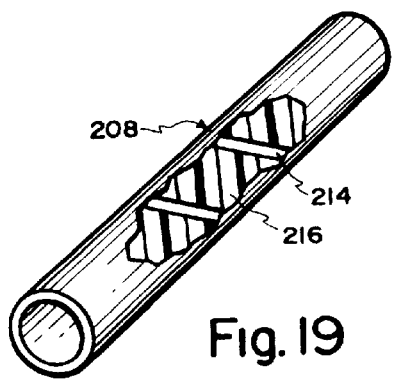
Fig. 19
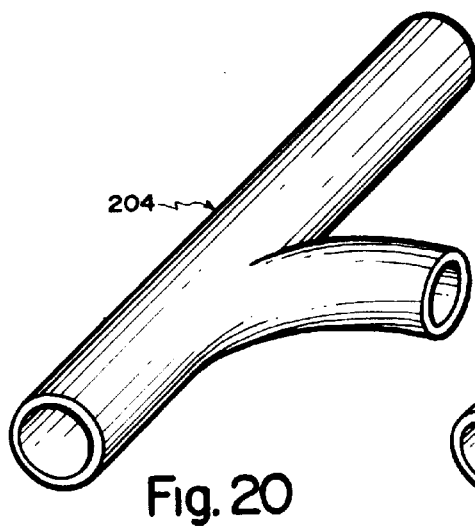
Fig. 20
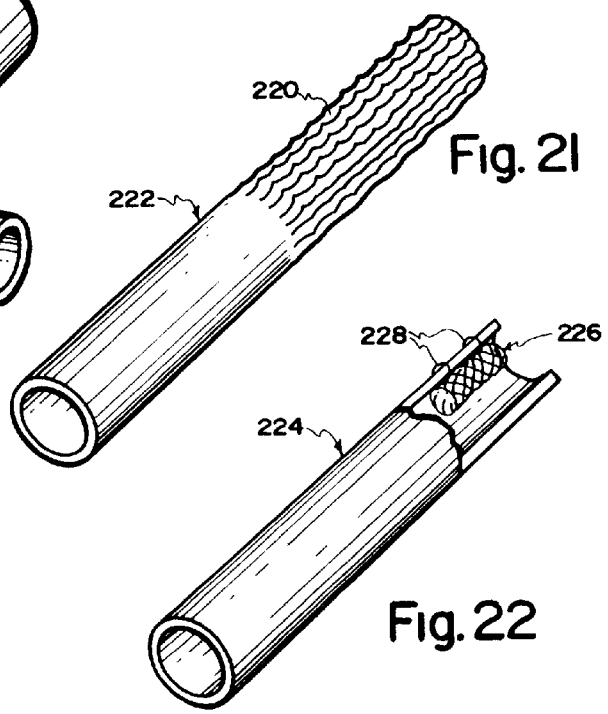
Fig. 21
Fig. 22

METHOD FOR INCREASING BLOOD FLOW IN VESSELS

CONTINUITY

This application is a division of pending U.S. patent application Ser. No. 08/073,002, filed Jun. 7, 1993, now U.S. Pat. No. 5,571,169 which is a continuation-in-part of U.S. patent application Ser. No. 08/056,224, filed May 4, 1993, now abandoned, which is a continuation of U.S. patent application Ser. No. 07/922,115, filed Jul. 28, 1992, now U.S. Pat. No. 5,282,484, which issued Feb. 1, 1994, which is a continuation of U.S. patent application Ser. No. 07/616,240, filed Nov. 20, 1990, now abandoned, which is a division of U.S. patent application Ser. No. 395,500, filed Aug. 18, 1989, now abandoned.

FIELD OF THE INVENTION

The present invention relates generally to restoration of flow capacity to occluded and partially occluded vessels, including arteries, and more particularly to a procedure by which at least an interior lining is in the form of a vascular graft placed in an artery as an anti-stenotic measure.

BACKGROUND

During the last thirty (30) years the most common technique for treating arterial stenosis has been surgical construction of a bypass conduit around the site of the occlusion. Bypass grafting in a symptomatic patient with a partially or totally occluded or stenotic superficial femoral artery, using a vein or prosthetic graft, has been the dominant technique for arterial reconstruction. Endarterectomy is also performed in some cases.

In the last decade balloon catheter angioplasty of patients with focal stenosis has demonstrated benefit primarily because of its minimal invasiveness, thereby reducing cost and recovery time. It is, however, limited to short focal stenoses through which the balloon can be positioned. It has a significant rate of restenosis in longer or diffuse lesions, where its use is not indicated. To address these limitations and to improve the treatment of longer length segments of occlusive disease, a variety of catheter based laser and mechanical atherectomy devices have recently been developed and studied. The hope has been to obtain the benefits of reducing costs, morbidity, and recovery time available from using less-invasive, catheter-based methods while still obtaining the overall good patient results comparable to by-pass grafting. Despite these efforts, by-pass grafting has remained the technique generally used in clinical practice, due to its superior overall results compared to the novel catheter-based techniques heretofore developed. The present invention overcomes or substantially alleviates the limitations of previous catheter-based techniques for treating SFA disease, while obtaining the benefits of proven by-pass grafting techniques.

BRIEF SUMMARY AND OBJECTS OF THE INVENTION

In brief summary, the present invention overcomes or substantially alleviates the above-mentioned pre-existing problems. The present invention provides for removal of all or nearly all atheroma from within an arterial segment of any length and then placement of a vascular graft, which may be of any suitable material, with only one point of entry. The atheroma alone can be removed or the atheroma and the tunica intima alone or together with the tunica media of the arterial segment can be removed. Other vessels can also be treated and vascularly lined without departing from the scope of the invention. The present invention provides the benefits of minimally invasive surgery, overcomes or substantially alleviates the limitation of recurrent stenosis, and allows treatment of any occlusive lesion regardless of length.

Thus, normal capacity blood flow is provided with no or low probability of recurring stenosis. While the present invention has been applied to occlusion in the superficial femoral artery, it is not limited to any particular artery diseased by stenosis.

With the foregoing in mind, it is a primary object of the present invention to provide an antistenotic method and product by which substantially full blood flow capacity is restored to a wholly or partially occluded artery.

Another object of importance is the provision of a method and product by which an atheroma is removed from an artery and provision is made to prevent or alleviate the likelihood of a later redevelopment of another atheroma at the removal site.

A further significant object is to provide a method and product by which substantially full blood flow is surgically restored to a stenotic artery.

Another dominant object is the provision of a method and product which substantially eliminates an atheroma from an artery and eliminates or significantly reduces the likelihood of restenosis at the prior atheroma site.

An additional object of substantive importance is the provision for removal of stenotic deposits from an artery with or without removal of an interior portion of the artery followed by insertion of a vascular graft along the length of the removal site as an anti-stenosis measure.

One more object of value is the provision of a method of and product for substantially removing stenotic deposits in an artery and substantially preventing or alleviating recurrence thereof independent of the arterial length of the deposits.

An additional paramount object is the provision of a novel method and product by which a vessel of a medical patient is lined for the purpose of establishing and/or maintaining full blood flow.

These and other objects and features of the present invention will be apparent from the detailed description taken with reference to the accompanying drawings.

BRIEF DESCRIPTION OF THE DRAWINGS

The Figures described briefly below are line drawing schematics, predicated upon the existence and commercial availability of the various devices and apparatus as shown therein.

FIG. 8 is a line drawing diagrammatically illustrating in cross-section removal of the tunica intima endothelium and tunica media collectively from an artery at a natural interface of weakness existing between the tunica media and the tunica adventitia;

FIG. 16 is a line drawing diagrammatically illustrating in perspective one suitable pre-formed cylindrical or sleeve-shaped vascular graft for lining arteries in accordance with the present invention;

FIG. 17 is a line drawing diagrammatically illustrating in perspective a tapered, pre-formed vascular graft for carrying out the present invention;

FIG. 18 is a line drawing diagrammatically illustrating in perspective, with parts broken away for clarity, the utilization of a vascular graft, pre-formed and cylindrical or sleeve-shaped in configuration, having internal ring reinforcements;

FIG. 19 is a line drawing diagrammatically illustrating in perspective, with parts broken away for clarity, a vascular graft, pre-formed and cylindrical or sleeve-shaped in configuration, having internal helically-shaped reinforcement, for carrying out the present invention;

FIG. 20 is a line drawing diagrammatically illustrating in perspective a bifurcated vascular graft for carrying out the present invention;

FIG. 21 is a line drawing diagrammatically illustrating in perspective a vascular graft, pre-formed and cylindrical or sleeve-shaped in configuration, having tissue in-growth material along a portion of the exterior surface thereof;

FIG. 22 is a line drawing diagrammatically illustrating in perspective, with a portion broken away for clarity, a vascular graft, pre-formed and cylindrical or sleeve-shaped in configuration, having an expandable stent internally sutured at the distal end thereof in the contracted state, for carrying out the present invention;

FIG. 38 is a line drawing diagrammatically illustrating in cross-section a vascular graft secured at its distal end in an artery using an expanded stent;

FIG. 39 is a line drawing diagrammatically illustrating in cross-section placement of a coating on the treated interior surface of an artery to form in place a vascular graft.

FIG. 41 is a line drawing diagrammatically in cross-section the partially inflated balloon catheter and vascular graft after placement in a treated artery.

DETAILED DESCRIPTION OF THE ILLUSTRATED EMBODIMENTS

Introduction

Figure 1:
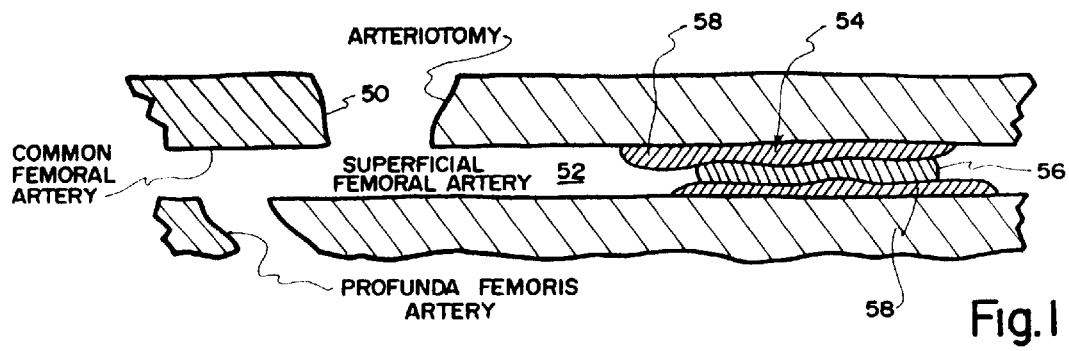
FIG. 1 is a line drawing diagrammatically illustrating in cross-section a single arteriotomy in an occluded superficial femoral artery of a medical patient.

The illustrated embodiments demonstrate and are representative of methods by which a partially or totally occluded artery or other vessel of a patient is recanalized and the risk of restenosis is substantially reduced or eliminated by use of a vascular graft within the treated artery.

While the present invention may be used in a vessel other than an artery, the primary benefit lies in application to an artery. Artery flow is either conduit or branch flow. The iliac, femoral, and more distal arteries are most likely to occlude, either totally or partially. All arteries are strong, durable, three-layer vessels while veins are thin, single layer conduits. The arterial wall layers are, inside out, the tunica intima endothelium (intima), the tunica media (media), and the tunica adventitia (adventitia). It has been found that in diseased arteries typically the interface between the adventitia layer and the media layer becomes a region of naturally occurring weakness. In fact, it has been found that plaque not only accumulates within the lumen of the artery but infiltrates both the intima and media causing a tissue breakdown there.

Removal of the intima and the media from the adventitia and leaving the adventitia of the artery is called an endarterectomy.

The primary cause of artery occlusion is build-up of plaque, the density of which ranges between very soft to rock-hard calcified deposits. Plaque deposits may form in some arteries and not at all or slightly in other arteries of the same person. A plaque deposit in a specific area or region of an artery is sometimes called an atheroma.

Under appropriate anesthesia the artery is exposed, clamped, and at least a single arteriotomy is performed distal to the clamp and proximal to the occlusion. Under some circumstances two arteriotomies are performed, one upstream and the other downstream of the atheroma although a single arteriotomy is preferred. In some situations access to the artery can be by use of percutaneously placed hollow needle, instead of by use of an arteriotomy.

In situations where an arteriotomy is the preferred choice, a guide wire is advanced through an upstream arteriotomy until the guide wire extends beyond the atheroma. Sometimes a guide wire can be advanced through a clogged artery, but not always. In situations where a guide wire alone cannot cross the atheroma, a dynamic wire guide or a dynamic disrupter is preferably used to centrally loosen and/or displace the centrally disposed plaque followed by central insertion of the guide wire through the hollow interior in the dynamic wire guide or disrupter. Thereafter, the dynamic wire guide or disrupter is removed.

Any technique by which the plaque is severed from the inner wall of the intima is called an atherectomy. Typically, plaque may be so severed by a coring catheter or by using an atherotome having one or more expandable blades to accommodate insertion and one or more passes through the atheroma, each pass at an increased blade diameter.

Atherectomy devices such as a Simpson Atherocath, an Auth Rotablator, a Kensey device, or an Intervertional Technologies Transluminal Extraction Catheter (TEC device) may be used.

In some situations an endarterectomy is the preferred medical choice. For example, an endarterectomy is often best when the disease of the artery is substantially advanced, causing a natural interface of weakness between the media and the adventitia. A cutting atherotome may be used to initially cut through the diseased intima and media to the adventitia at the distal end of the site of the endarterectomy creating a taper at that location followed by advancement in a proximal direction until the entire undesired length of intima and media have been excavated. Alternatively, the intima and media may be cut radially or on a bevel adjacent both a first and second arteriotomy located above and below the atheroma. Ideally, a taper is used at both ends of the endarterectomy where the enlarged lumen produced connects across a beveled tapered to the normal lumen of the artery, both distally and proximally the dispensed material is loosened from the wall using any suitable instrument, such as a surgical spatula. Forceps may be used to grasp and pull upon a loosened part of the intima and media to be removed causing the intima and media between the two cuts together with the atheroma contained therein to be removed from the artery as a cylindrical unit.

Alternatively, a Hall loop may be advanced from one arteriotomy to the other after the two above-mentioned cuts have been made. The loop, in the nature of a piano wire loop held on the end of a staff is positioned at the above-mentioned natural interface of weakness. The loop is positioned at and displaced along the interface by pushing on the staff until the intima, the media, and the atheroma to be removed have been unitarily severed following which the cylindrical unit may be grasped and removed from the artery using forceps, for example.

Similarly, a Scanlan Endarsector or a cutter having rotating blades may be used to assist in the performance of the endarterectomy.

In situations where an angioplasty, in whole or in part, is the treatment of choice, an instrument of expansion is used to enlarge or open and enlarge the blood flow accommodating lumen at the atheroma. Mechanical instruments, equipment for performing balloon angioplasty, laser instruments, and instrumentation for ultrasound angioplasty may be used to achieve the angioplasty.

Once the plaque has been excavated, steps are taken to line the remaining treated arterial or vessel wall. The resulting lining is herein referred to as a vascular graft. Vascular graft, as used herein, is intended to mean any of the following: 1. conventional and novel artificial grafts made of any material, including but not limited to fabrics such as dacron, or expanded PTFE Gortex™ thin wall sleeve material, in any density from very soft and low density to very stiff and high-density, constructed in any shape including straight, tapered, or bifurcated, and which may or may not be reinforced with rings and spirals or other reinforcement, and which may or may not have one or more expandable stents incorporated into the graft at one or both ends or along its length, 2. natural artery or vein material taken from human or animal donors, 3. stents, 4. coating applied to the inside of the treated arterial wall which forms a patent lumen or is biologically active and causes the lining of the vessel or duct to form a patent lumen, and 5. any combination of the foregoing vascular graft options. The exterior of the vascular graft or part of it may and preferably does comprise tissue in-growth material. Where a preformed tubular vascular graft of synthetic material is used, the material thereof may be and preferably is dimensionally stable. However, if desired, it may be radially expandable material.

The vascular graft of choice may be introduced into the treated artery or other vessel in any suitable way including but not limited to use of a dilator/sheath, placement of the vascular graft upon a mandrel shaft and/or use of long-nose forceps. The distal ends of the tubular graft and the mandrel shaft may be temporarily sutured together or the distal end of the vascular graft sutured together over the mandrel to accommodate unitary displacement into the vessel, for example through a sheath after the dilator has been removed.

Where the material of which the vascular graft is formed is expandable and in tubular or sleeve form, once the sheath has been removed the diametral size of the graft may be enlarged in contiguous relationship with the inside arterial surface using a balloon catheter. A balloon catheter may also be used to bring a folded or partially collapsed vascular graft which is dimensionally stable into contiguous relation with the interior surface of the remaining artery wall.

The tubular graft may also comprise a biologically inert or biologically active anti-stenotic coating applied directly to the treated area of the remaining arterial inner surface to define a lumen of acceptable blood flow capacity.

The graft, once correctly positioned and contiguous with the interior vascular wall, is usually inherently secure against inadvertent migration within the artery or other vessel due to friction and infiltration of weeping liquid accumulating on the inside artery wall. It is preferred that the length of the vascular graft be selected to span beyond all of the treated region of the artery.

One or both ends of the vascular graft may be sutured or surgically stapled in position on the treated wall to prevent undesired displacement or partial or complete collapse under cardiovascular pressure. In particular, the upstream end of a graft placed in an artery must be secure to prevent a flap of the graft from being pushed, by arterial blood flow, into a position where it occludes, in whole or in part, the vessel. One or both ends may be held open by one or more stents disposed within the tubular graft. Forceps may be used to hold a free end of the vascular graft while the other end is secured to the vascular wall. Currently, it is preferred to secure the proximal end of the tubular vascular graft to the treated vascular wall and to bias dilate the distal end of the tubular vascular graft by use of a balloon catheter and/or arterial pressure. Where the distal exterior of the sleeve-shaped vascular graft comprises tissue in-growth material, as is preferred as in-growth occurs it becomes immaterial how the initial dilating bias was achieved.

The Illustrated Embodiments

Reference is now made to the drawings wherein like numerals are used to designate like parts throughout. While the drawings are specifically directed toward the removal of an atheroma in the superficial femoral artery, it is to be appreciated that the principles of the present invention apply to other arteries as well as to ducts and vessels in the body other than arteries. Specifically, FIG. 1 illustrates the juncture between the common femoral artery and the superficial femoral artery and profunda femoris artery, respectively located at a site near the groin of a medical patient. FIG. 1 further illustrates the existence of a surgically created arteriotomy 50 providing access to the superficial femoral artery 52 at a location proximal of an atheroma, generally designated 54. The atheroma 54 comprises a centrally located, relatively soft central plaque portion 56 surrounded by a calcified plaque portion 58.

Figure 2A:
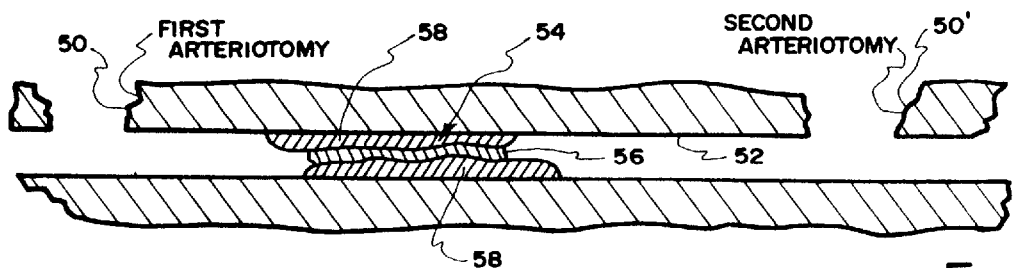
FIG. 2A is a line drawing schematically illustrating in cross-section a double arteriotomy in an occluded superficial femoral artery of a medical patent.

FIG. 2A is similar to FIG. 1 and further illustrates a second arteriotomy 50' located distal of the atheroma 54, providing a second access site to the artery 52, as explained herein in greater detail.

Figure 2B:
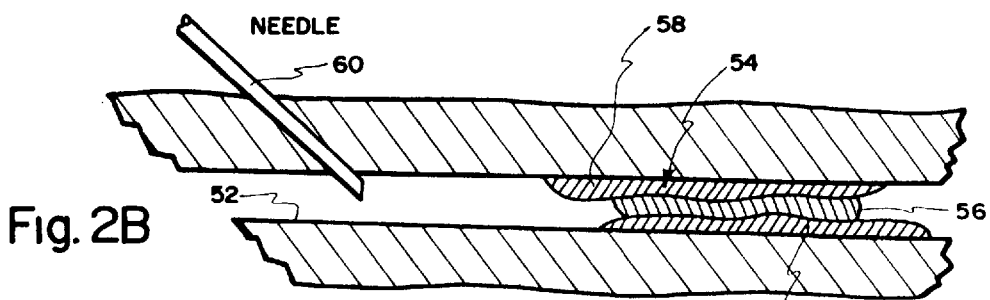
FIG. 2B is a line drawing schematically illustrating in cross-section access using a hollow needle to a site upstream of an atheroma in a superficial femoral artery of a patient.

FIG. 2B illustrates the same artery 52 to which access is provided solely by percutaneous placement of a needle 60 into the hollow of the artery 52 upstream (proximal) of the atheroma 54. Needle 60 accommodates plaque removal and placement of a lining within the artery 52.

While FIGS. 1, 2A, and 2B illustrate an atheroma which completely occludes the artery 52, it is to be appreciated that the present invention applies to both partial and complete occlusion due to plaque. The overall objective is to restore substantially full blood flow to the artery and prevent restenosis. It is to be appreciated that the artery receiving treatment is temporarily deprived of blood flow altogether, using known methods of temporary occlusion. Prior to temporary occlusion, systemic or regional heparinization may be effected.

Figure 3:
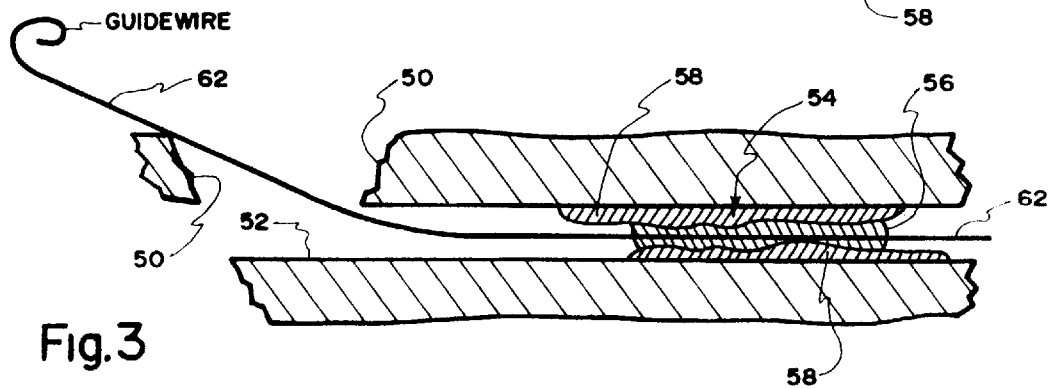
FIG. 3 is a line drawing diagrammatically illustrating in cross-section the atheroma of FIG. 1 with a guide wire extending through the atheroma.
Figure 4:
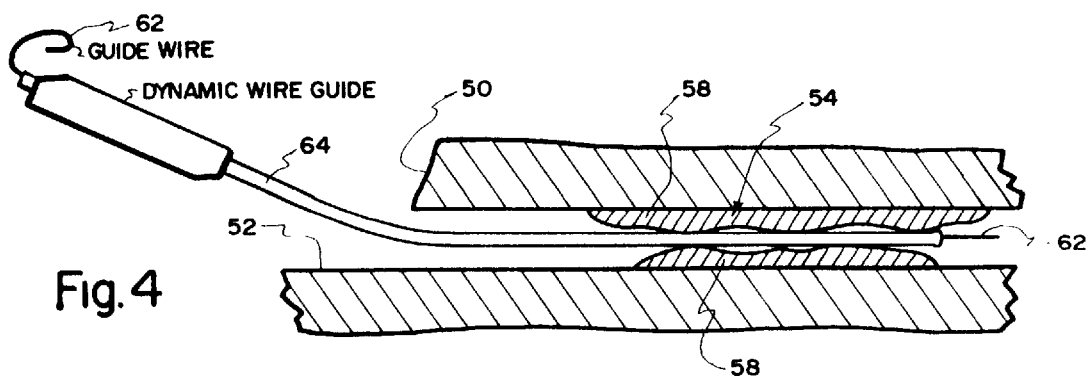
FIG. 4 is a line drawing diagrammatically illustrating in cross-section placement of a dynamic wire guide through the arteriotomy sufficient for the distal region of the dynamic wire guide to extend completely through the atheroma accommodating passage of a guide wire through a lumen in the dynamic wire guide before the dynamic wire guide is withdrawn.

Typically, as illustrated in FIG. 3, after the arteriotomy 50 has been made near the origin of the superficial femoral artery, a guide wire 62, conventional in construction, is advanced distally through the arteriotomy 50 and through the atheroma 54 along the softer plaque portion 56 thereof. If the guide wire 62 alone cannot be manually caused to traverse the atheroma 54, as illustrated in FIG. 3, other medical instruments may be used to create a passageway through the atheroma 54 following which the guide wire 62 may be appropriately inserted so as to traverse the atheroma 54. For example, a dynamic wire guide 64 may be advanced and operated so as to create a lumen through the softer plaque 56 of the atheroma 54 as diagrammatically illustrated in FIG. 4. Currently, the preferred dynamic wire guide is the one disclosed in pending U.S. patent application Ser. No. 07/973,514, filed Nov. 9, 1992, assigned to EndoVascular Instruments, the assignee of the present application, although other dynamic and static wire guides could be used.

Once the dynamic wire guide 64 has penetrated the central plaque region 56 so as to traverse the hard plaque portion 58, the guide wire 62 is advanced through the lumen within the dynamic wire guide 64, following which the dynamic wire guide is withdrawn leaving the guide wire 62 in position, as a guide for instruments by which the soft and hard plaque 56 and 58 are removed.

Figure 5:
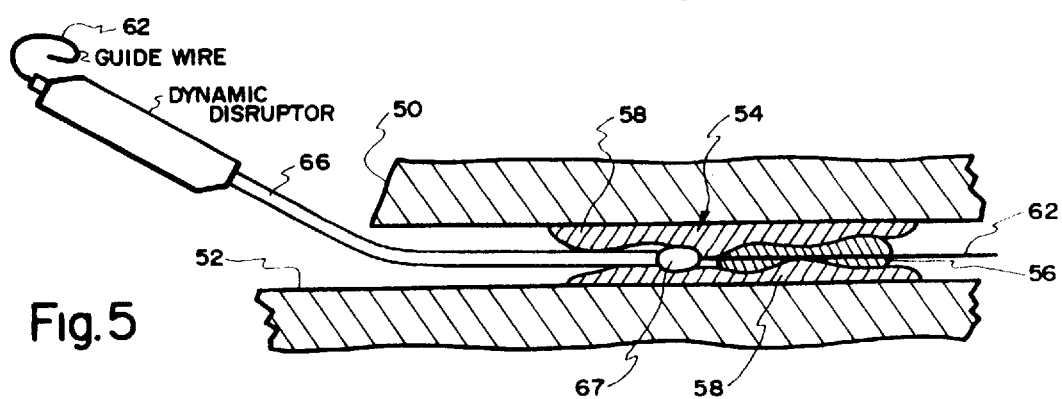
FIG. 5 is a line drawing diagrammatically illustrating in cross-section the advancement of a dynamic disrupter, over a guide wire for traversing the stenotic obstruction site in the superficial femoral artery.

Alternatively, with reference to FIG. 5, a dynamic disrupter 66, having a rotating enlarged rounded tip 67, may be used in lieu of the dynamic wire guide described above to penetrate the softer plaque region 56 sufficient to accommodate concentric insertion of the guide wire 62 through the dynamic disrupter 66, with the dynamic disrupter 66 after being removed along the guide wire while the guide wire is retained in its inserted position. Currently, the preferred dynamic disrupter is the one disclosed in pending U.S. patent application Ser. No. 07/973,514, filed Nov. 9, 1992, assigned to EndoVascular Instruments, the assignee of the present application, although other dynamic disrupters could be used.

While not shown, it is to be appreciated that plaque, separated from the atheroma 54, cannot be allowed to remain uncollected within the artery and, therefore, conventional instruments and procedures are used appropriately downstream of the atheroma 54 to collect and remove all debris released during treatment of the atheroma 54.

Figure 6:
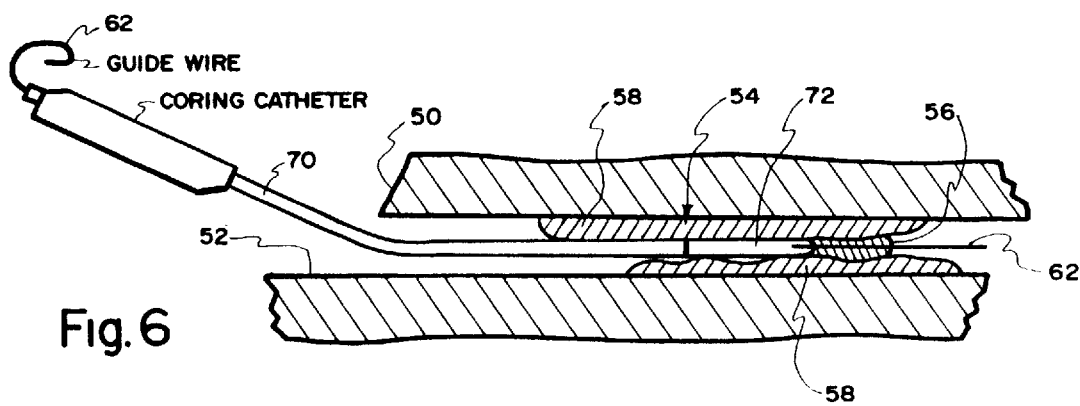
FIG. 6 is a line drawing diagrammatically illustrating in cross-section the advancement of a coring catheter along a guide wire spanning the atheroma obstruction in the artery to enlarge the lumen by removal of plaque.
Figure 7:
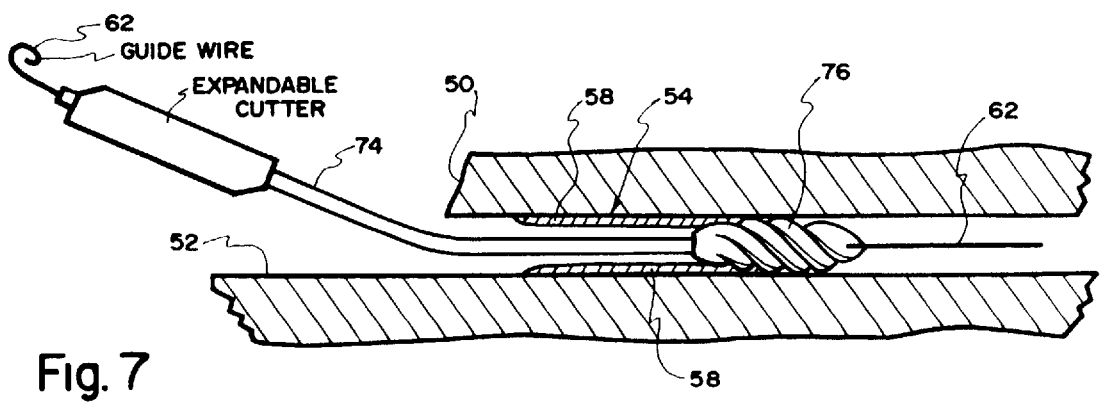
FIG. 7 is a line drawing diagrammatically illustrating in cross-section the artery showing an expandable cutting catheter or atherotome displaceable along the guide wire and expansion of blades of the cutter so as to cut plaque from the atheroma, using as many passes as appropriate with or without flushing or irrigating of the lumen.

Having established the appropriate placement of guide wire 62 through the atheroma 54, the surgeon is in a position to enlarge the arterial lumen at the site of the atheroma 54 by removing plaque 58. Such removal is commonly referred to as an atherectomy. The severing, grinding, cutting, chipping, and abrading of the plaque 58 may be mechanically accomplished by any suitable cutting instrument. Exemplary types are illustrated in FIGS. 6 and 7, respectively. FIG. 6 illustrates diagrammatically utilization of a coring catheter 70, advanced along the guide wire 62 through the arteriotomy 50 so as to cut the plaque 58 from the artery 52 using as many passes along the atheroma 54 as necessary. The coring catheter has a cutting head 72 which is caused to be rotated by the surgeon. It is currently preferred that the coring catheter 70 be that which is disclosed in the assignee's co-pending U.S. patent application Ser. No. 07/973,514, which was filed Nov. 9, 1992, although any suitable coring catheter may be utilized.

Either in conjunction with a coring catheter or in lieu thereof, the lumen across the atheroma 54 can be enlarged using an expandable cutter, having diametrally expandable cutting blades as illustrated in FIG. 7. The expandable cutter 74 is initially advanced along the guide wire 62 in an unexpanded state. Expandable cutter 74 has a diametrally adjustable cutting head 76 which, when expanded and pulled forward atherectomy 50 will cut or shave the plaque at deposits 58. Alternatively, the expandable cutter may be utilized in a fashion in which the expandable cutting blades, when expanded, engage and grab hold of a section of the plaque. When the expandable cutter is pulled, it both cuts the junction with the remaining distal plaque and allows a cylindrical length of the plaque which lies proximal of the cutting blades to be removed all in one segment. Typically, a plurality of passes of the cutting head 76, each with a slightly greater diameter are required to completely excavate plaque 58. Currently, it is preferred that the expandable cutter disclosed in assignee's U.S. Pat. No. 5,211,651 be utilized.

Attention is now turned to those situations where an endarterectomy is the procedure of choice. Specific reference is now made to FIG. 8 which illustrates, in part, one way in which the intima 100 and the media 102 are collectively separated from the adventitia 104 along a natural interface of weakness 106, which typically exists in diseased arteries. A first and second arteriotomy 50 and 50' may be made proximal and distal of the atheroma and a radial or tapered cut at or near each arteriotomy made through the intima and media layers to the interface 106. By loosening a length of the two interior layers 100 and 102 of the artery 52 from the adventitia along the interface 106 at the radial or beveled cut adjacent the arteriotomy 50, the loosened part is available for grasping, using a suitable instrument such as forceps 108 illustrated in FIG. 8. By pulling one or more times in the general direction of arrow 110 so as to have a substantial axial-component along the length of the artery 52, the cut length of intima and media is severed along interface 106 and pulled from the artery through arteriotomy 50.

While not illustrated in all of the Figures (for simplicity of presentation), it is to be appreciated that all arteries comprise three layers, the intima, the media, and the adventitia.

It is to be understood that the distinction between atherectomy and endarterectomy is somewhat arbitrary, as it depends upon whether the material being removed consists exclusively of atheroma only, or of a combination of atheroma and material characteristic of the inner lining of the vessel. Pathology analysis of such removed material frequently indicates the presence of cells and other material characteristic of both plaque and the media and intima, so it is probably most correct to refer to this procedure as an endarterectomy.

In one currently preferred embodiment, an endarterectomy is performed using the dynamic disrupter and the expandable cutter. The dynamic disrupter is first advanced over the guide wire both to loosen the plaque and the intima and media along the natural interface of weakness, and to enlarge the channel or lumen through the artery. The dynamic disrupter may be advanced one or more times. If multiple advances are used, the repeated advancements may be done using the same tip size, or they may be done using successively larger tip sizes.

After the dynamic disrupter has been used and withdrawn over the guide wire, the expandable cutter is employed to remove the material that has been loosened. With the blades unexpanded, the expandable cutter is advanced a suitable distance into the atheromatous region, and then the blades expanded. When the expandable cutter is withdrawn, it engages the plaque and arterial lining, and exerts force upon the natural interface of weakness. The plaque and arterial lining are withdrawn by the expandable cutter in the form of a cylindrical plug of material, which may be short or long depending upon how far into the plaque the cutter is advanced before it is expanded. After removing the plug of material from the cutter, the blades are returned to the unexpanded position and re-advanced into the artery, this time to a position further than the previous advancement, so that a new length of atheromatous material can be engaged. The blades are once again expanded, and a new plug of material is engaged and withdrawn. By a repeated series of such steps, any desired length of artery may be excavated of its plaque and inner lining. When the final advance to the most distal point is performed, the distal tapered shape that the blades assume when expanded leaves behind the desired tapered shape as it cuts and removes the final plug of material from the artery. This eliminates any need to make the second arteriotomy 50', for the purpose of making the distal radial cut, when the expandable cutter is employed.

Figure 9:
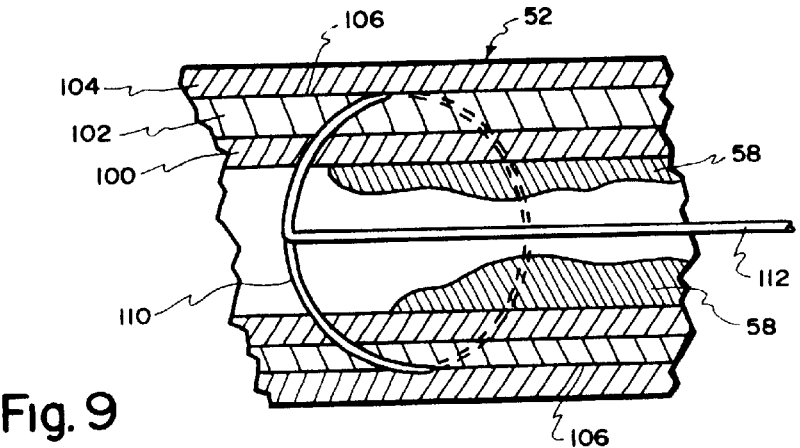
FIG. 9 is a line drawing diagrammatically illustrating in cross-section separation of a length of the tunica intima endothelium together with the tunica media from the tunica adventitia along a natural interface of weakness using a Hall loop.

In the alternative, an endarterectomy may be performed using a Hall loop, as diagrammatically illustrated in FIG. 9. Preliminarily, the artery containing the atheroma 54 is accessed, as illustrated in FIG. 2A, by first and second arteriotomies 50 and 50'. The first radial or beveled cut through the intima and media is made, as described above, and the media is severed along interface 106 at one end or the other (usually the upstream, proximal end) for a short distance to allow the loop 110 to be placed at the interface, with the flexible shaft 112 extending in the direction of the pull and through the more remote arteriotomy. When power is applied, the loop is caused to oscillate as the Hall loop is advanced along the interface 106 until complete severance has occurred, following which forceps may be used to pull the removed intima and media layers from the artery through the proximal arteriotomy after the second radial or beveled cut through the intima and media is made, attempting to leave a tapered contour to the remaining material at the distal end of the endarterectomy. The Hall loop is more fully described in U.S. Pat. No. 3,730,185.

Figure 11:
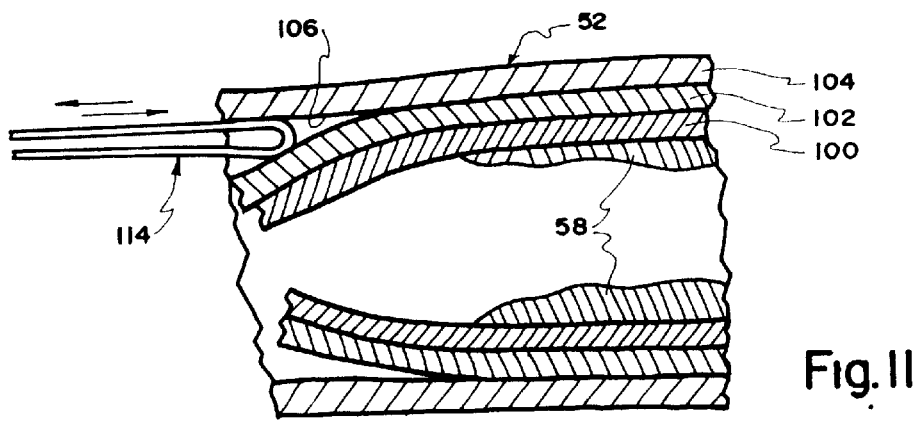
FIG. 11 is a line drawing diagrammatically illustrating in fragmentary cross-section use of a Scanlan Endarsector to separate conjointly a length of the tunica intima endothelium and tunica media from the tunica adventitia along a natural interface of weakness.

The endarterectomy may similarly be performed using a Scanlan Endarsector, as generally illustrated in FIG. 11. It is to be appreciated that the Scanlan Endarsector 114 is a commercially available instrument, sold by Scanlan International, Inc., 1 Scanlan Plaza, St. Paul, Minn. 55107, and may be used alone or in conjunction with other instruments to perform the endarterectomy. The Scanlan Endarsector 114 comprises a handle (not shown) from which an elongated U-shaped shaft extends. By probing with the Scanlan Endarsector along the interface 106 adjacent portions of the media 102 and intima 100 which have been loosened, further loosening occurs until the endarterectomy is completed and the severed artery portion removed.

Reference is now made to FIGS. 12 through 15 which illustrate various ways in which an atherectomy may be performed when that procedure is the treatment of choice, in whole or in part, for enlarging the blood flow lumen of artery 52 at atheroma site 54.

Figure 12:
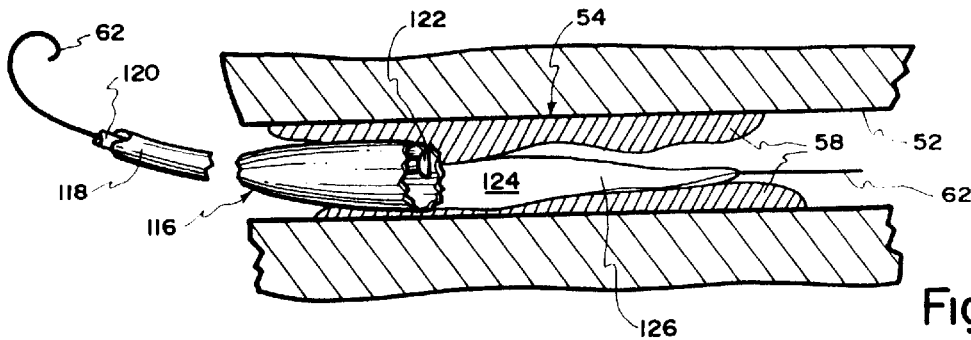
FIG. 12 is a line drawing diagrammatically in cross-section a Simpson Atherocath performing an atherectomy.

With specific reference to FIG. 12, there is illustrated a mechanical instrument for the performance of an atherectomy, i.e., Simpson Atherocath, generally designated 116. The atherocath comprises an outside, hollow shaft 118 through which extends a rotatable inner shaft 120 to which a rotating cutter head 122 is non-rotatably attached. The rotating cutting head 122 cuts plaque 58 from the interior of the artery 52 as the atherocath is advanced. A balloon 124 is inflated on the side opposite the cutting head 122 to thereby bring pressure to bear against the artery and urge the cutting head firmly against the plaque. At the distal end of the atherocath is located a chamber 126, which functions to collect plaque shavings removed by the cutting head 122. The atherocath 116 is inserted and removed along guide wire 62. The Simpson Atherocath is commercially available from Devices for Vascular Intervention, division of Eli Lilly, 26201 YNEZ Road, Temecula, Calif. 92591.

Figure 13:
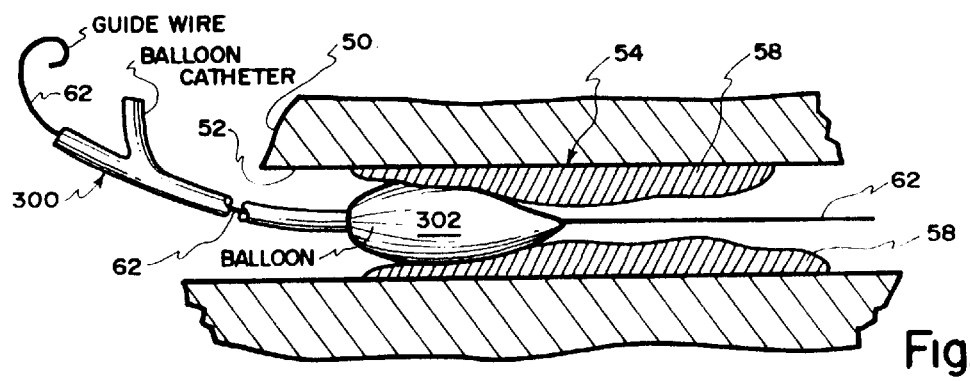
FIG. 13 is a line drawing diagrammatically illustrating in cross-section performance of a balloon angioplasty.

FIG. 13 diagrammatically represents the use of balloon angioplasty to enlarge the lumen of an atheroma-ridden artery. Specifically, a balloon 302 of a balloon catheter 300 is advanced along guide wire 62 until it is disposed within the atheroma 54. Using the side port of the balloon catheter 300, the balloon 302 is expanded, which radially expands the plaque 58. This process ordinarily creates cracks in the plaque, but nevertheless results in an enlarged lumen through the plaque 58 although, typically, the plaque 58 is not intentionally removed.

Figure 14:
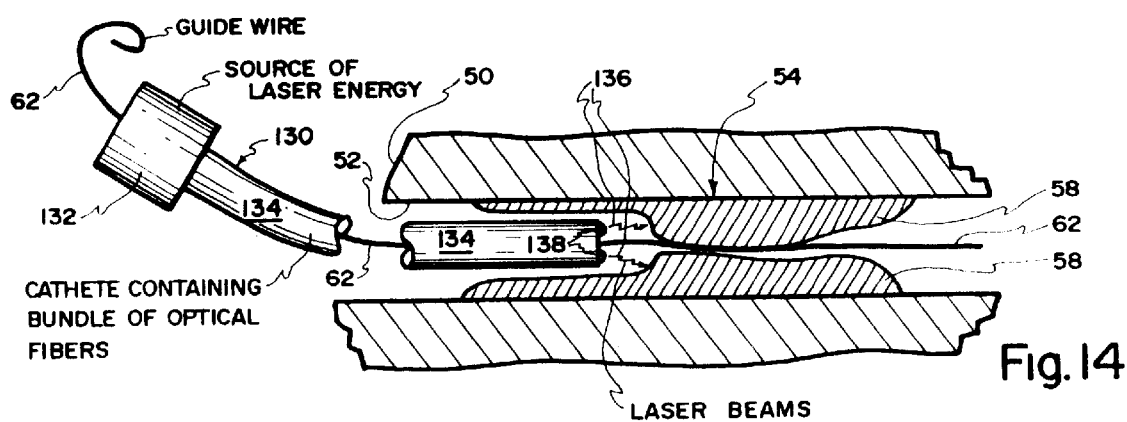
FIG. 14 is a line drawing diagrammatically illustrating in cross-section the performance of an atherectomy using a laser.
Figure 15:
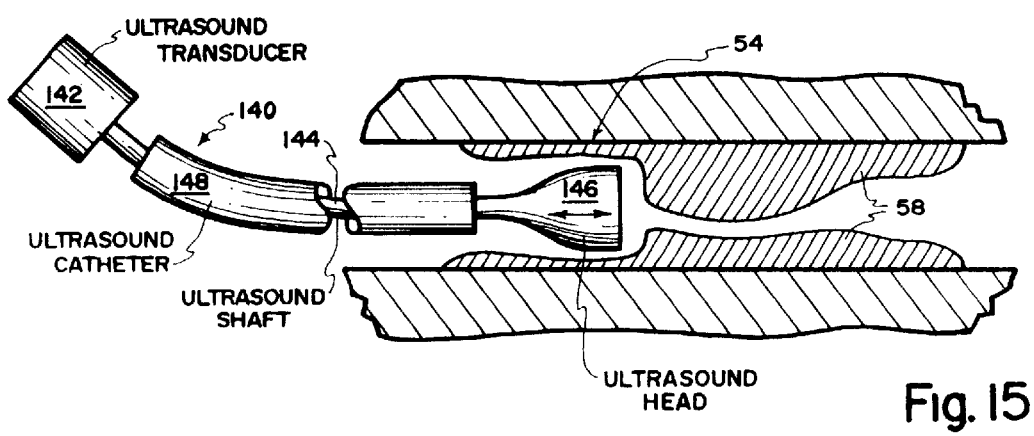
FIG. 15 is a line drawing diagrammatically illustrating in cross-section performance in an artery of ultrasound angioplasty.

Reference is now made to FIG. 14 which diagrammatically illustrates use of a laser instrument, generally designated 130 to remove plaque 58 from artery 52. The laser instrument 50 comprises a source 132 of laser energy. The laser energy is processed along a bundle of optical fibers disposed within a catheter 134. Laser beams 136 are emitted from the instrument 130 through a plurality of laser emitters 138. The laser beams 136 cut plaque from deposits 58 as the distal end of the catheter 134 is advanced distally into the plaque 58. The laser instrument 130 is illustrated as being concentrically disposed upon guide wire 62 for insertion, advancement, and ultimate removal. Thus, an atherectomy may be performed in accordance with the principles of the present invention by use of one or more laser beams. A suitable laser instrument is the Laserprobe PLR or Lasercath-PRL, used with the Optilase Laser Source System, all of which are available from Trimedyne, Inc., 1815 East Carnegie Avenue, Santa Ana, Calif. 92705.

In lieu of the above-mentioned ways for performance of an atherectomy, or in conjunction therewith, ultrasound energy may be used. Specific reference is made to FIG. 15 which illustrates diagrammatically an ultrasound instrument, generally designated 140. Instrument 140 comprises a source of ultrasound energy, i.e., ultrasound transducer 142. Transducer 142 connects via an ultrasound shaft 144 to an ultrasound head 146. The ultrasound shaft 144 is substantially concentrically disposed within an ultrasound catheter 148. A guide wire is not used. Release of ultrasound energy from head 146 is caused to impinge upon plaque 58 fracturing the same progressively, thereby enlarging the blood flow lumen of the artery 52. A suitable ultrasound instrument for removal of plaque is the Sonocath, available from Angiosonics, Wayne, N.J., (201) 305-1770.

Once the interior of the partially or totally occluded artery has been treated using an appropriate procedure including one or more of the procedures described above, the present invention includes placement of a lining or vascular graft so as to extend preferably co-extensively along the full length of the treated portion of the artery. The nature of the vascular graft will vary depending upon the circumstances, the artery in question, the length over which the artery has been treated, and perhaps other factors. The vascular graft may be of any suitable biologically inert material including, but not limited to, a dacron sleeve of medical grade fabric, a sleeve of expanded PTFE (such as GOR-TEX® polytetrofluoroethelene vascular graft tubing available from W. L. Gore and Associates, Inc., Medical Products Division, 1505 N. 4th Street, Central Dock 3, Flagstaff, Ariz. 86002). Another available sleeve formed of expanded PTFE is available from IMPRA, Inc., P.O. Box 1740, Tempe, Ariz. 85280-1740.

The material may be dimensionally stable or capable of being expanded, for example, using a balloon catheter and/or one or more stents. For short lengths, vascular graft 200 (FIG. 16) may be used. Vascular graft 200 is illustrated as having blunt ends, is cut to a length commensurate with the treated artery and comprises exterior and interior surfaces respectively comprising a uniform diameter along the entire length of the vascular graft 200. The wall thickness is also illustrated as being uniform.

For longer lengths, tapered vascular graft 202 (FIG. 17) may be preferable, the degree of taper being selected so as to match the taper of the artery subjected to one or more of the treatments described above.

In cases where the artery being lined is bifurcated (e.g., comprises a branch from one to two arteries), vascular graft 204 (FIG. 20) may be used, the configuration thereof being adapted to conform specifically to the nature of the shape, size, and disposition of the branched artery subjected to treatment. Depending upon the anatomy, vascular graft 204 may be straight or tapered or straight in part and tapered in part.

When strength greater than the mere material from which a vascular graft is formed becomes a consideration, the vascular graft may be reinforced, particularly when no expansion thereof is required during placement. Two typical forms of reinforcement are illustrated in FIGS. 18 and 19, respectively, which depict vascular graft 206 and vascular graft 208, respectively. Vascular graft 206 comprises reinforcement in the form of a plurality of rings 210. While illustrated as being embedded within the material 212 from which the vascular graft 206 is formed, the reinforcing rings could be placed either internally or externally in respect to the graft 206 itself.

Similarly, vascular graft 208 is illustrated in FIG. 19 as comprising a continuous, helical reinforcement 214 embedded in the material 216 from which the vascular graft 208 is formed. The reinforcement 214 could be placed as well either internally or externally of the vascular graft 208 itself.

The reinforcement, e.g., rings 210 and helix 24 can be of any suitable biologically inert material such as an implantable grade of thermoplastic material, e.g., polypropylene or nylon.

Even in cases where sutures, staples, and/or stents are used to initially hold the lining or vascular graft contiguously against the treated artery wall, utilization of tissue in-growth material at the exterior of all or part of the vascular graft may be desirable. In this regard, specific reference is made to FIG. 21 which diagrammatically illustrates the existence of tissue in-growth material 220 disposed along approximately the distal one-half of the hollow cylindrically-shaped vascular graft 222. The value of the tissue in-growth material is that it becomes, in due course of time, the primary connector between the treated arterial surface and the vascular graft.

With reference to FIG. 22, there is diagrammatically illustrated a hollow cylindrical vascular graft 224 to which an expandable stent 226 has been connected interiorly at the proximal end thereof using sutures 228. Once the vascular graft 224 is properly positioned within a treated artery, the stent 226 is conventionally expanded to bias the proximal end of the vascular graft 224 contiguously against the treated arterial surface to retain the position of placement. This condition is illustrated in FIG. 38. While illustrated as being placed internally inside of graft 224, the stent could also be placed externally or it could be embedded within the material from which the vascular graft 224 is formed.

Utilization of a vascular graft within the context of the present invention significantly tends to provide a barrier between the bloodstream and the vessel wall which is believed to reduce restenosis, provides a conduit through which the blood can flow which is known to be well-tolerated by the bloodstream, preserves the area available for blood flow, prevents an aneurysm, promotes rapid healing without excessive weeping or adhesion of blood at the lining site between the vascular graft and the adventitia layer, and provokes minimal scarring. Plaque, it has been determined, does not form on and adhere to the vascular graft.

In lieu of a pre-formed straight or tapered sleeve (with or without a bifurcation) the treated arterial wall, e.g., at interface 106, may be lined using a liquid coating of suitable material applied as a spray or otherwise and allowed to cure until a hollow lumen is defined within the cured coating and the treated arterial surface is concealed by the coating, or allowed to remain in place long enough to cause the artery to form a stable, hollow lumen. In this regard, reference is made to FIG. 39 which illustrates the presence of a manually controlled nozzle 230 forming a part of a surgical spraying instrument by which a coating 232 is applied to the treated arterial surface at interface 106. Suitable coatings, for example, having the requisite biologically inert characteristics and wall adherence characteristics would include pharmaceutical-grade collagen available from Collagen Corp., 1850 Embariadero Road, Palo Alto, Calif. 94303.

Figure 23:
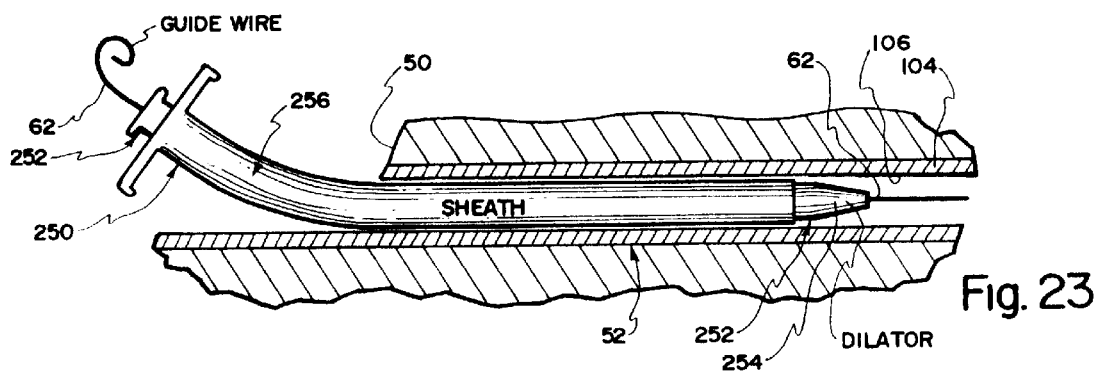
FIG. 23 is a line drawing diagrammatically illustrating in cross-section placement of a dilator/sheath along a guide wire into the artery for placement of a vascular graft.
Figure 24:
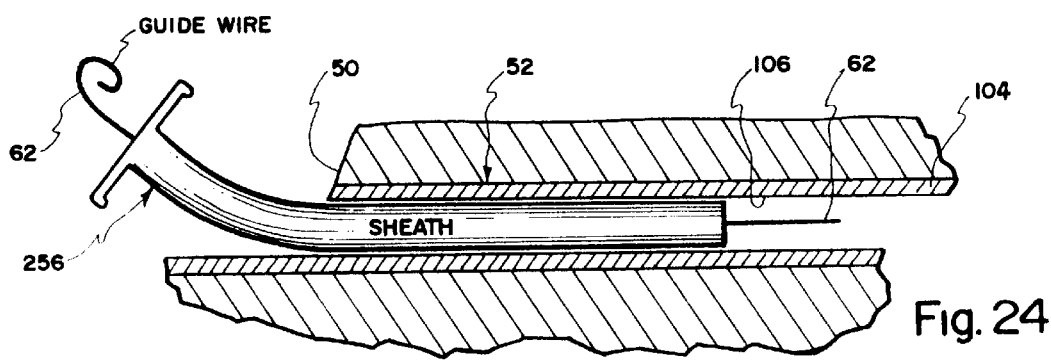
FIG. 24 is a line drawing diagrammatically illustrating in cross-section the sheath of FIG. 23 with the distal portion thereof in the artery after the dilator has been removed.

Once the vascular graft of choice has been selected, other than an in-place coating, insertion of the vascular graft into the treated artery must be achieved. It is currently preferred to use a commercially available dilator/peel-away sheath generally designated 250 (FIGS. 23, 24, 26, and 27). However, a solid (non-peel-away) sheath may also be utilized or the graft may be inserted directly into the vessel without use of a sheath. As is well known in the art, the dilator/sheath 250, in assembled condition, is passed concentrically along the guide wire 62 through the access opening to the artery 52. The access opening may be an arteriotomy 50 or a percutaneous venipuncture caused by insertion of needle 60 (FIG. 2B) followed by advancement of the guide wire through the needle 60 and subsequent removal of the needle. In the case of a needle puncture, the dilator 252 at the tapered distal tip 254 enlarges the radial size of the puncture as does the sheath 256 (slightly) as the dilator-sheath 250 is advanced through the puncture concentrically around the guide wire 62 until the dilator-sheath 250 is positioned as illustrated in FIG. 23. Once the position of FIG. 23 has been achieved, the medical attendant simply manually retracts the dilator along the guide wire 62 until it is fully removed, leaving the sheath 256 in place with the proximal end thereof exposed, as diagrammatically illustrated in FIG. 24.

Figure 25:
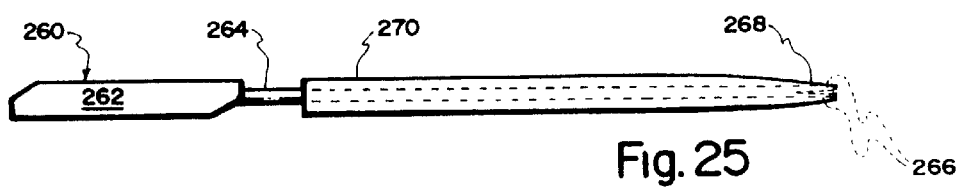
FIG. 25 is a line drawing diagrammatically illustrating in elevation a vascular graft placement mandrel having a vascular graft attached to the mandrel shaft for placement in an artery.
Figure 26:
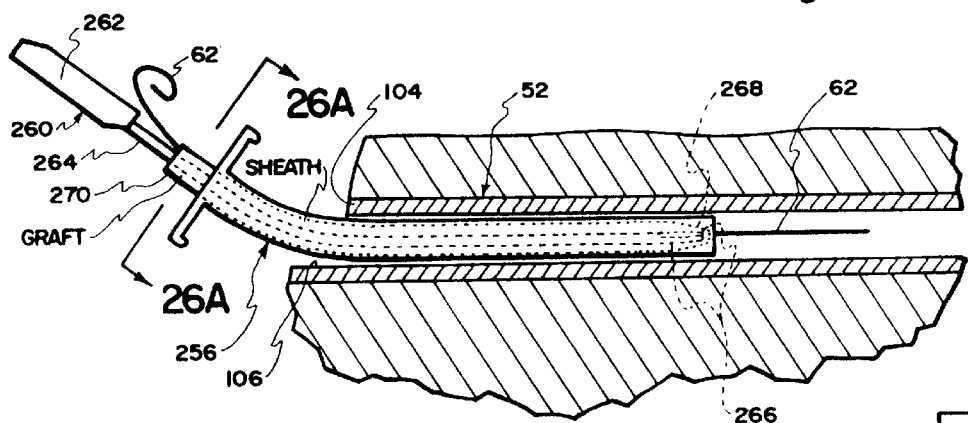
FIG. 26 is a line drawing diagrammatically illustrating in cross-section of the vascular graft and the distal end of the mandrel of FIG. 25 being advanced into the artery through the sheath of FIG. 24.
Figure 27:
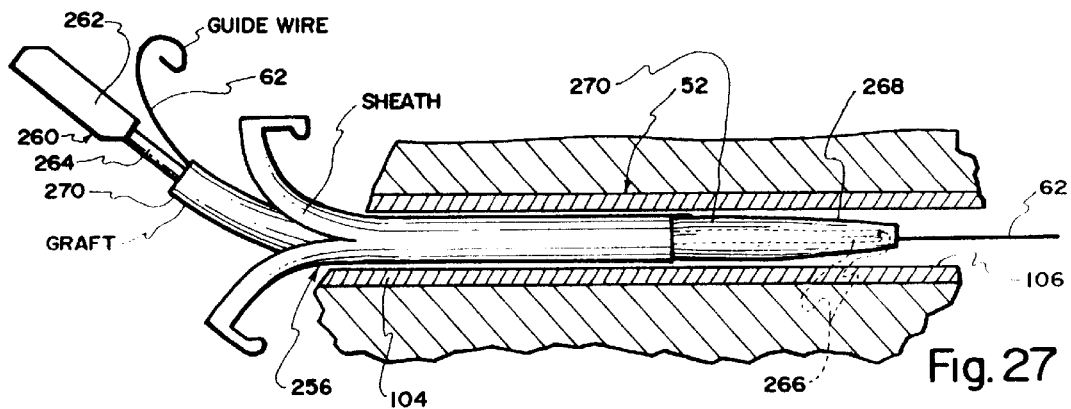
FIG. 27 is a line drawing diagrammatically illustrating in cross-section partial removal of the sheath of FIG. 25 after the distal end of the mandrel shaft and the vascular graft has been placed in the desired position in the artery through the sheath, with the graft being held by the mandrel while the sheath is withdrawn.

Next, steps are taken to insert the vascular graft through the sheath and locate the graft in the treated artery so as to be, preferably, at least co-extensive with the treated artery surface, with the guide wire inside the graft. The treated artery surface shown in FIGS. 23–24 and 26–27 is interface 106. One way in which insertion may be consummated is by use of a graft placement long-nose forceps, generally designated 260 (FIG. 25) which comprises a control handle 262 from which a mandrel shaft 264 distally extends. Activation of the control 262 causes bifurcated tips 266 located at the distal end of the mandrel shaft 264 to open and close, to grasp or clamp and release, respectively, the distal end 268 of a hollow tubular vascular graft 270. By grasping between tips 266 the distal end 268 of the vascular graft 270, the vascular graft follows the mandrel shaft 264 as it is advanced over the guide wire 62 and through the sheath 256 as illustrated in FIGS. 26 and 27.

With the graft 270 correctly positioned in the artery 52, the forceps 260 and graft 270 are held in a stationary position, the forceps grasping the graft, as the sheath is withdrawn. In the case of peel-away sheath 256, as the sheath is withdrawn it is manually split into two pieces, as illustrated in FIG. 27, following which each piece is discarded.

At this point, the forceps 260 and the graft 270, with the guide wire 62 passing centrally through the graft, are left in position and the sheath 256 has been entirely removed. Thereafter, the guide wire and graft 270 are held stationary, the mandrel control 262 manipulated to open the tips 266 causing the distal end 268 of the graft 270 to be released, following which the forceps 260 are withdrawn while the guide wire 62 and the graft 270 are retained in position as illustrated in FIG. 28.

Figure 34:
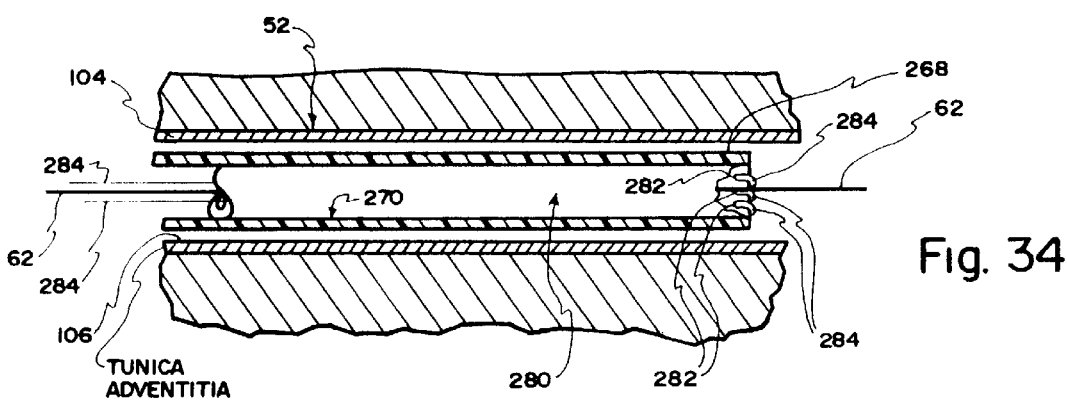
FIG. 34 is a line drawing diagrammatically illustrating in cross-section a vascular graft, sutured at the distal end thereof to the distal end of a mandrel both disposed in a treated artery.

Alternatively, the sheath may be placed correctly in the artery 52 using a hollow mandrel, generally designated 280 (FIG. 34). Wherein the sheath 270 is concentrically disposed around the hollow mandrel 280 with the distal ends of each being sutured together using apertures 282 located in the distal end of the mandrel 280. By placing a suture 284 helically through the apertures 282 and through the adjacent thickness of the vascular graft 270, the vascular graft and the mandrel are secured together. Where only one access opening, such as arteriotomy 50, is used, the suture 284 may be extended through the hollow of the mandrel 280 and through the arteriotomy 50 for access by the medical attendant. Once fully positioned in the artery, one end of the suture 284 is pulled by the medical attendant, causing the suture to helically unwind at the distal end of the vascular graft 270 for complete removal of the suture 284, following which the mandrel 280 is fully retracted leaving the vascular graft 270 correctly disposed in the artery 52, with the guide wire 62 inside the graft.

Figure 35:
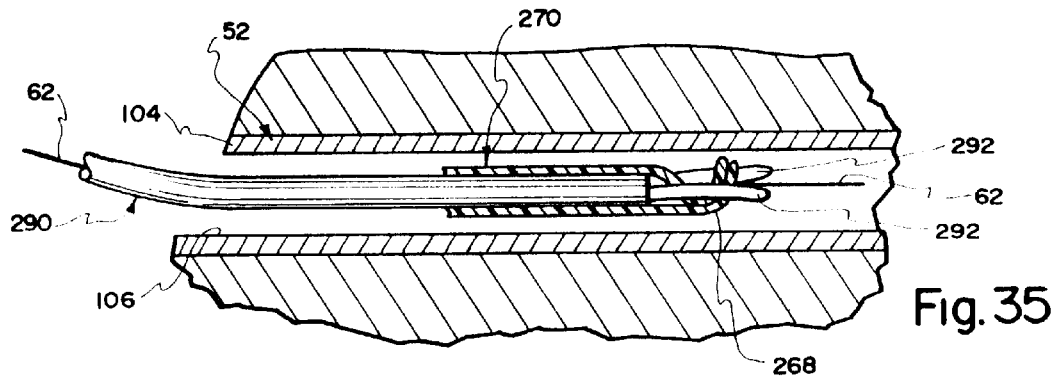
FIG. 35 is a line drawing diagrammatically illustrating in cross-section placement of the distal end of a vascular graft in an artery by use of a placer/suturer.

Similarly, with or without a dilator/sheath, used in the manner described above, an elongated, long-nose forceps 290 (FIG. 35) may be used as well for correct placement of the vascular graft 270. Long-nose forceps 290 may be of any suitable type, such as commercially available pediatric bronchoscopy forceps or retrieval forceps, such as Storz's. More specifically, the forceps 290 comprise exposed jaws 292 which are controlled at the proximal end of the forceps 290 accommodating opening and closing of the jaws 292. By creasing or folding at 268 the vascular graft 270 and forcing the crease or fold 268 between the jaws 292 when open accommodates clamping of the creased distal end 268 when the jaws 292 are tightly closed. Thereafter, the forceps 290 and the vascular graft 270 are jointly advanced through the access site, such as arteriotomy 50, until the vascular graft 270 is correctly located in the treated artery 52, as illustrated in FIG. 35. Thereafter, the jaws 292 are opened, the fold 268 at the distal end of the vascular graft 270 is released and the forceps 290 retracted leaving the vascular graft 270 properly disposed within the artery 52.

Figure 28:
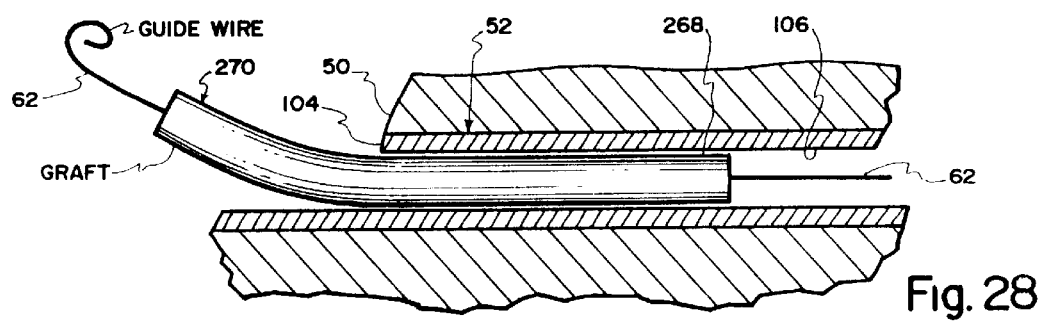
FIG. 28 is a line drawing diagrammatically illustrating in cross-section the existence of the vascular graft in the artery after both the sheath and the mandrel have been removed therefrom.

Independent of the procedure used, the vascular graft 270 is now correctly located in the artery 52, with the guide wire 62 passing through the center of the vascular graft 270, as illustrated in FIG. 28.

Figure 26A:
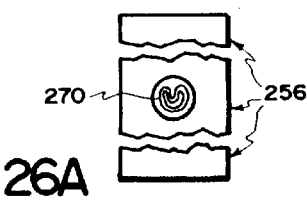
FIG. 26A is a cross-section taken along line 26A—26A of FIG. 26.
Figure 29:
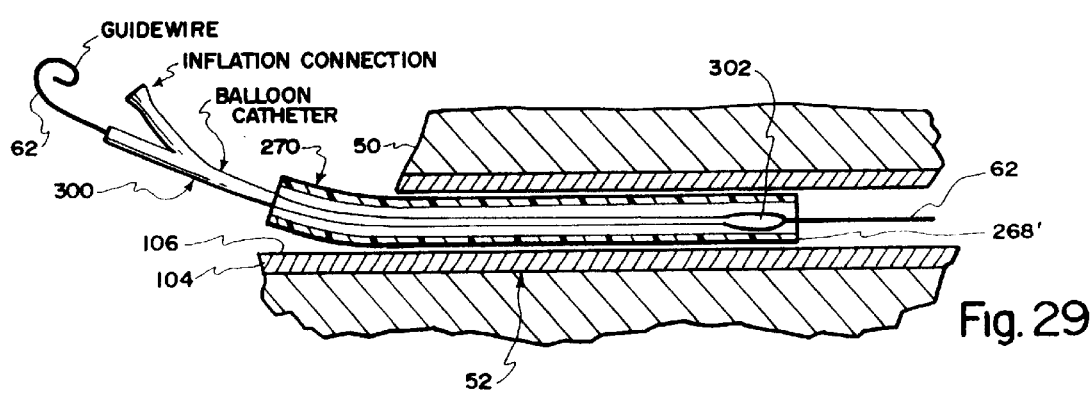
FIG. 29 is a line drawing diagrammatically illustrating in cross-section a balloon catheter disposed in the vascular graft after the graft has been positioned as illustrated in FIG. 28.

Insertion of a tubular graft of choice into the treated artery often involves folding or other forms of reduction in the diametral size occupied by the vascular graft during insertion, for example, to accommodate a size which will allow displacement through the sheath 256. The sheath handle may accept a graft folded shown in FIG. 26A. This folded configuration may continue the length of the sheath, to allow the easier passage of the graft through the sheath, by de-forming the inside diameter to the shape, or by laying a conventional catheter or wire alongside the graft during insertion to create an indentation in the graft. For this reason and because, typically, the walls of a synthetic vascular graft are very supple and lack shape-retaining strength, the vascular graft, if left alone, tends to be and remain non-contiguous with the treated surface at the interior of the artery, e.g., surface 106, e.g., retaining the crimped or folded shape it assumes during insertion. In order to provide a contiguous relationship between the vascular graft and the adjacent arterial wall and to dilate the vascular graft to its full diameter, it is presently preferred that a balloon catheter 300 of conventional, commercially available design be advanced concentrically around the guide wire 62 until the balloon 302 thereof is positioned within the sheath 270 just inside the distal edge 268' of the sheath 270. See FIG. 29.

Figure 30:
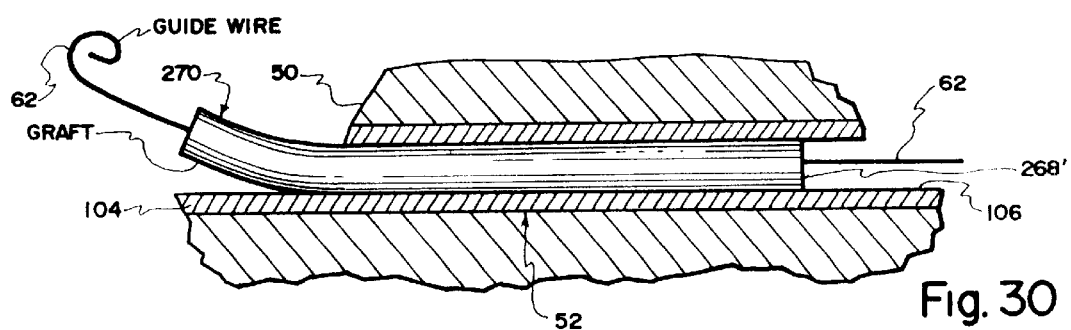
FIG. 30 is a line drawing diagrammatically illustrating in cross-section the vascular graft firmly contiguous with the inside surface of the artery after the vascular graft has been expanded by use of the balloon catheter illustrated in FIG. 29 and the balloon catheter but not the guide wire has been removed.

By sequentially expanding, deflating, slightly displacing and once more inflating, etc., the balloon 302, the vascular graft 270 is caused to become contiguous with and adhered to the adjacent arterial wall surface, following which the balloon 302 is deflated and the balloon catheter 300 retracted along the guide wire and discarded, leaving the vascular graft 270 postured as illustrated in FIG. 30. Alternatively, one very long balloon catheter can be employed to perform this step in a single balloon expansion, and/or the balloon can be sized to exactly match the graft, e.g., tapered balloon used with tapered graft, etc.

Figure 31:
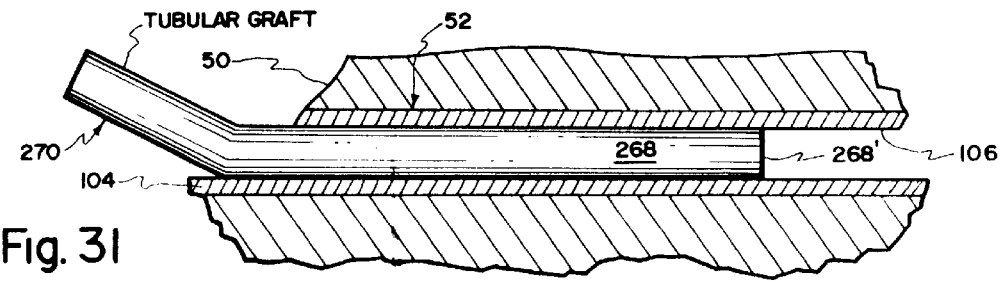
FIG. 31 is a line drawing diagrammatically illustrating in cross-section the disposition of the vascular graft in the artery after all other paraphernalia has been removed.

Thereafter, the guide wire 62 is fully retracted, leaving the tubular vascular graft 270 positioned as essentially illustrated in FIG. 31. It has been found that once the tubular vascular graft is firmly contiguous with the adjacent arterial wall surface, a measure of friction exists which both prevents radial collapse and axial displacement of the vascular graft within the artery. In addition, the treated arterial surface tends to weep slightly which weeping adheres to the exterior surface of the tubular graft and tends to infiltrate the material from which the tubular graft is formed at least to a limited extent further causing the graft to be retained in its expanded stationary position, fully dilated within the artery.

Figure 32:
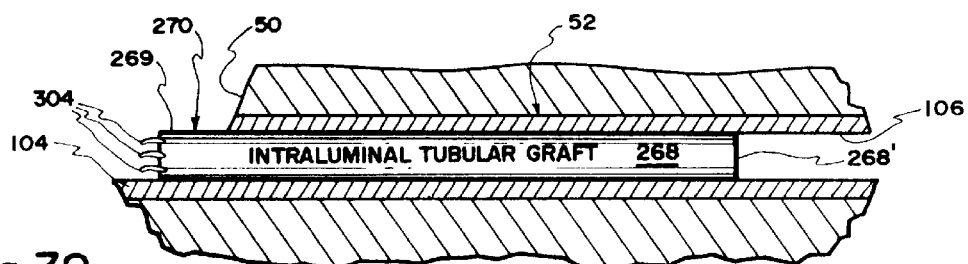
FIG. 32 is a line drawing diagrammatically illustrating in cross-section the vascular graft of FIG. 32 linearly disposed within and sutured proximally near the wall of the superficial femoral artery.

As best illustrated in FIG. 32, it is presently preferred that only the proximal end 269 of the vascular graft 270 be physically connected to the adjacent arterial wall, in this case adventitia layer 104, and that the distal end 268 be left to natural adherence, with the arterial blood pressure holding the distal end 268 in its fully dilated position together with friction at the surface 106 and tissue infiltration into the material from which the graft 270 is fabricated. In FIG. 32 the utilization of one or more sutures 304 is illustrated as the structure by which the proximal end 269 of the vascular graft 270 is physically secured to the arterial wall.

Figure 10:
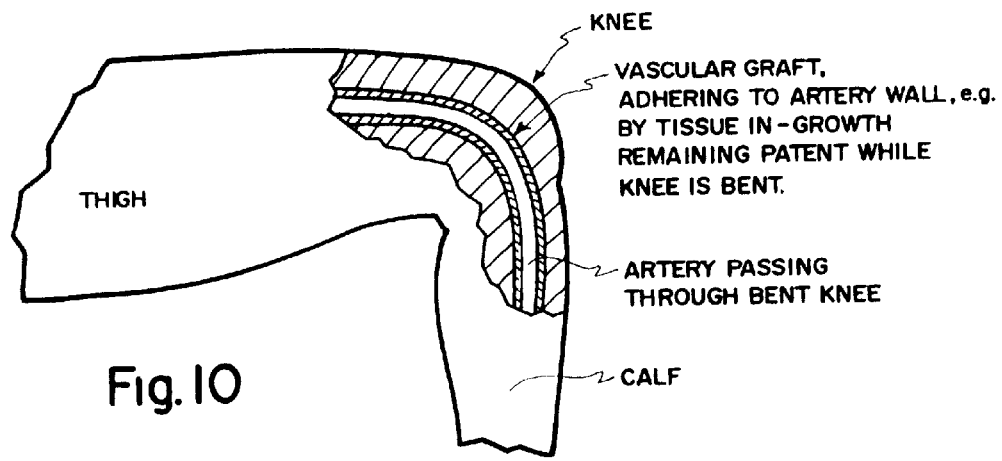
FIG. 10 is a line drawing diagrammatically illustrating in cross-section a vascular graft according to the present invention having collapse resistant characteristics placed in the knee of a patient.

Over the longer term, the graft will be held open and contiguous with the remaining original wall of the artery throughout its length by arterial blood pressure and, in grafts so constructed, by tissue in-growth into the tissue in-growth material. This particular feature of intra-luminal graft placement solves a specific problem of by-pass graft placement where by-pass grafts have previously been placed in tissue tunnels constructed to by-pass the original duct or vessel lumen. Many such grafts are placed in body regions where, under normal activities, the body tends to compress grafts and thereby cut off flow through such grafts when they are placed in tissue tunnels which by-pass the original lumen. The example of the human knee joint is illustrated in FIG. 10. Convention placement of by-pass grafts, which pass through the knee joint, results in the surrounding tissue tending to compress the graft and cut off flow when the knee is bent. Conventionally, this problem has been solved by using a reinforced graft, as previously illustrated in FIGS. 18 and 19, wherein the reinforcing holds the graft lumen open and patent when external tissue pressure is exerted on the graft.

An improved result is obtained using the intra-luminal graft placement described herein is illustrated in FIG. 10. The original artery lumen remains open and patent in the knee even when the knee is bent. More generally, ducts and vessels naturally remain open and patent during the normal range of activities. In FIG. 10, the lumen of the graft, which is adhering to the remaining original wall of the artery by tissue in-growth and/or due to the arterial pressure inside the graft, is illustrated as remaining open and patent even while the knee is bent. More generally, intra-luminal grafts held in place in vessels or ducts by tissue in-growth will remain open and patent during the normal range of activities, including activities that tend to obstruct by-pass grafts placed in tissue tunnels.

Figure 36:
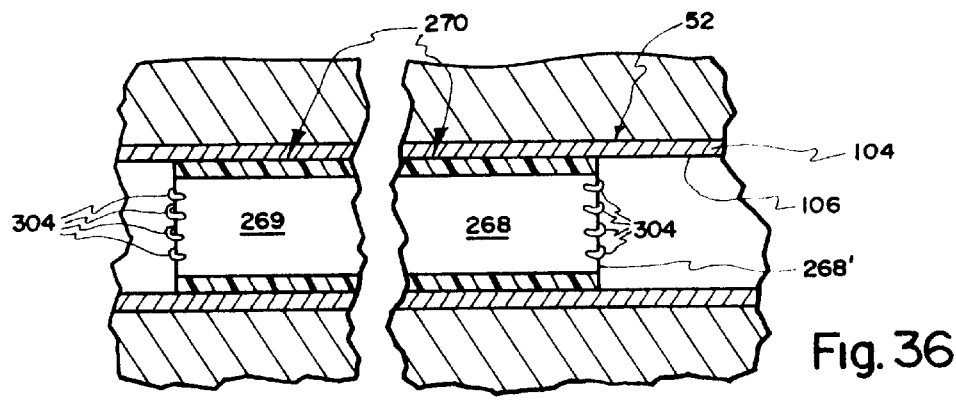
FIG. 36 is a line drawing diagrammatically illustrating in fragmentary cross-section the securing of both ends of a vascular graft in an artery using one or more sutures at each end.

While it is currently preferred that the distal end 268 of the vascular graft 270 be without manmade connection to the vascular wall, if desired the distal end 268 may be so secured. Specifically, FIG. 36 illustrates utilization of one or more sutures 304 to secure both the proximal and distal ends 269 and 268, respectively, of the vascular graft 270 to the arterial wall 104. Placement of sutures 304 at the distal end 268 of the vascular graft 270 would ordinarily require a second, downstream arteriotomy.

Figure 37:
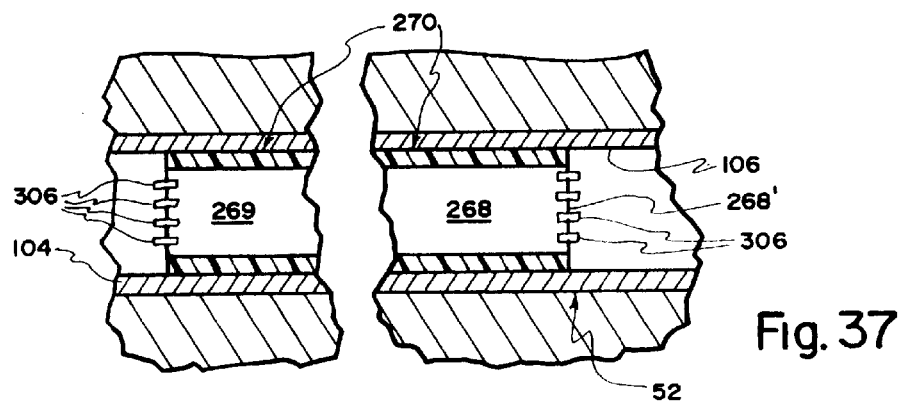
FIG. 37 is a line drawing diagrammatically illustrating in fragmentary cross-section securing of a vascular graft in a treated artery using staples at both the distal and proximal ends of the vascular graft.
Figure 40:
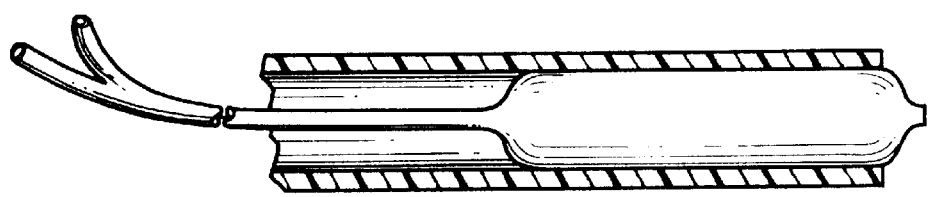
FIG. 40 is a line drawing diagrammatically in cross-section a balloon catheter having the balloon thereof partially inflated within a vascular graft prior to joint insertion into a treated artery.

Similarly, one or both ends of the vascular graft 270 may be secured to the arterial wall 104 using medical grade staples 306, as illustrated in FIG. 37.

Furthermore, either or both ends of the vascular graft 270 can be expanded and held in contiguous relationship with arterial surface 106 using one or more stents 226, as explained above and as illustrated in FIG. 38.

Figure 33:
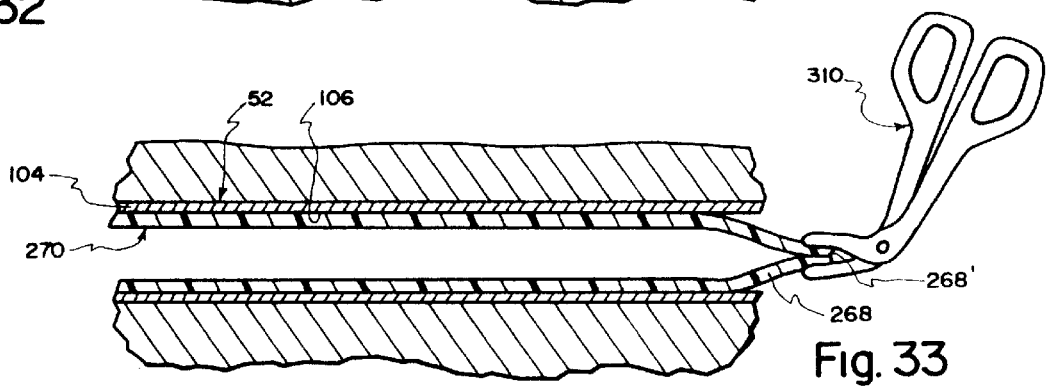
FIG. 33 is a line drawing diagrammatically illustrating in cross-section grasping of the distal end of a vascular graft in the treated artery using forceps.

While ordinarily not necessary, the distal end 268 of the vascular graft 270 may be grasped using suitable forceps 310 for both positioning the vascular graft 270 and for holding it in position while, for example, the proximal end of the graft is suitably fastened to the arterial wall as explained above. See FIG. 33.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of treating an artery, comprising the steps of:
   enlarging the lumen size of a plaque-ridden segment of an artery using a plaque-removing instrument introduced through an arteriotomy;
   clamping a vascular lining to a clamping instrument so that at least a substantial portion of an exterior surface of the lining is exposed;
   jointly inserting the lining and the clamping instrument into the artery through the arteriotomy to a position at least in part co-extensive with a portion of the segment;
   securing the vascular lining within said artery at said location.

2. A method according to claim 1 wherein the enlarging step comprises enlarging the lumen within the artery by performing plaque-removing angioplasty.

3. A method according to claim 1 wherein the enlarging step comprises first loosening and thereafter removing plaque through the arteriotomy.

4. A method according to claim 1 wherein the enlarging step comprises cutting plaque.

5. A method according to claim 1 wherein the enlarging step comprises chipping plaque.

6. A method according to claim 1 wherein the enlarging step comprises grinding plaque.

7. A method according to claim 1 wherein the enlarging step comprises applying laser energy to the plaque.

8. A method of treating an artery, comprising the steps of:
   enlarging the lumen size of a plaque-ridden segment of an artery comprising axially cutting and removing both plaque and a portion of the interior of the artery;
   placing a vascular lining within the artery at least in part co-extensive with a portion of the segment;
   securing the vascular lining within said artery at said location.

9. A method according to claim 1 wherein the enlarging step comprises applying ultrasound energy to disconnect plaque from the segment.

10. A method according to claim 1 wherein the enlarging step comprises excising pieces of plaque from the artery through the arteriotomy.

11. A method according to claim 1 wherein the enlarging step comprises grasping and tearing pieces of plaque from the artery.

* * * * *